US011198867B2

(12) United States Patent
Rigo et al.

(10) Patent No.: US 11,198,867 B2
(45) Date of Patent: Dec. 14, 2021

(54) COMBINATIONS FOR THE MODULATION OF SMN EXPRESSION

(71) Applicants: Ionis Pharmaceuticals, Inc., Carlsbad, CA (US); The Johns Hopkins University, Baltimore, MD (US)

(72) Inventors: Frank Rigo, Carlsbad, CA (US); C. Frank Bennett, Carlsbad, CA (US); Constantin Van Outryve D'Ydewalle, Baltimore, MD (US); Charlotte J. Sumner, Baltimore, MD (US)

(73) Assignees: Ionis Pharmaceuticals, Inc., Carlsbad, CA (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/307,092

(22) PCT Filed: Jun. 16, 2017

(86) PCT No.: PCT/US2017/037862
§ 371 (c)(1),
(2) Date: Dec. 4, 2018

(87) PCT Pub. No.: WO2017/218884
PCT Pub. Date: Dec. 21, 2017

(65) Prior Publication Data

US 2020/0308580 A1 Oct. 1, 2020

Related U.S. Application Data

(60) Provisional application No. 62/351,199, filed on Jun. 16, 2016.

(51) Int. Cl.
*C07H 21/04* (2006.01)
*C12N 15/113* (2010.01)
*C07H 21/02* (2006.01)

(52) U.S. Cl.
CPC ........... *C12N 15/113* (2013.01); *C07H 21/02* (2013.01); *C07H 21/04* (2013.01); *C12N 2310/11* (2013.01); *C12N 2310/315* (2013.01); *C12N 2310/322* (2013.01); *C12N 2310/3341* (2013.01); *C12N 2320/33* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 5,176,996 | A | 1/1993 | Hogan et al. |
| 5,256,775 | A | 10/1993 | Froehler |
| 5,294,564 | A | 3/1994 | Karapiperis et al. |
| 5,627,274 | A | 5/1997 | Kole et al. |
| 5,801,154 | A | 9/1998 | Baracchini et al. |
| 6,172,216 | B1 | 1/2001 | Bennett et al. |
| 6,210,892 | B1 | 4/2001 | Bennett et al. |
| 6,214,986 | B1 | 4/2001 | Bennett et al. |
| 6,376,508 | B1 | 4/2002 | Li et al. |
| 6,582,908 | B2 | 6/2003 | Fodor et al. |
| 6,753,423 | B1 | 6/2004 | Cook et al. |
| 6,770,633 | B1 | 8/2004 | Robbins et al. |
| 6,962,906 | B2 | 11/2005 | Efimov et al. |
| 6,998,259 | B1 | 2/2006 | Davis et al. |
| 7,034,009 | B2 | 4/2006 | Pavco et al. |
| 7,053,207 | B2 | 5/2006 | Wengel |
| 7,838,657 | B2 | 11/2010 | Singh et al. |
| 8,110,560 | B2 | 2/2012 | Singh et al. |
| 8,183,002 | B2 | 5/2012 | Adamczyk et al. |
| 8,361,977 | B2 | 1/2013 | Baker et al. |
| 8,586,559 | B2 | 11/2013 | Singh et al. |
| 9,717,750 | B2 | 8/2017 | Bennett et al. |
| 9,926,559 | B2 | 3/2018 | Bennett et al. |
| 10,436,802 | B2 | 10/2019 | Rigo et al. |
| 2001/0053519 | A1 | 12/2001 | Fodor et al. |
| 2003/0100505 | A1 | 5/2003 | Scharschmidt et al. |
| 2003/0228597 | A1 | 12/2003 | Cowsert et al. |
| 2005/0214288 | A1 | 9/2005 | Bell et al. |
| 2007/0031844 | A1 | 2/2007 | Khvorova et al. |
| 2007/0292408 | A1 | 12/2007 | Singh et al. |
| 2007/0299021 | A1 | 12/2007 | Dunckley et al. |
| 2008/0045456 | A1 | 2/2008 | Greenway et al. |
| 2008/0064084 | A1 | 3/2008 | Muller et al. |
| 2010/0081627 | A1 | 4/2010 | Sampath et al. |
| 2010/0087511 | A1 | 4/2010 | Singh et al. |
| 2011/0269820 | A1 | 11/2011 | Singh et al. |

(Continued)

FOREIGN PATENT DOCUMENTS

| | | | |
|---|---|---|---|
| EP | 1133993 A1 | 9/2001 | |
| WO | WO 1994/026887 | 11/1994 | |

(Continued)

OTHER PUBLICATIONS

Davis et al. "Potent inhibition of microRNA in vivo without degradation" Nucleic Acids Res (2009) 37: 70-77.
Khoo et al., "Splicing therapeutics in SMN2 and APOB" Curr Opin Mol Ther (2009) 11: 108-115.
Kiraly et al., "Expression of human cationic trypsinogen with an authentic N terminus using intein-mediated splicing in aminopeptidase P (pepP) deficient *Escherichia coli*" Protein Exp Purif (2006) 48: 104-111.
Koller et al., "Use of a Chemically Modified Antisense Oligonucleotide Library to Identify and Validate Eg5 (Kinesin-Like 1) as a Target for Antineoplastic Drug Development" Cancer Res (2006) 66: 2059-2066.
Miller et al., "Gene-Target Therapies for the Central Nervous System" Arch Neurol (2008) 65: 447-451.

(Continued)

*Primary Examiner* — Kimberly Chong
(74) *Attorney, Agent, or Firm* — McNeill Baur PLLC

(57) ABSTRACT

Certain embodiments are directed to methods and compounds for modulating expression of SMN. In certain embodiments at least two compounds are used: a first compound for inhibiting SMN-NAT and increasing expression of SMN, and a second compound for modulating the splicing of SMN. Such methods and compounds are useful for increasing expression exon 7 containing SMN mRNA in cells and animals.

37 Claims, No Drawings

Specification includes a Sequence Listing.

(56) References Cited

U.S. PATENT DOCUMENTS

| | | | |
|---|---|---|---|
| 2011/0294868 | A1 | 12/2011 | Monia et al. |
| 2012/0021515 | A1 | 1/2012 | Swayze et al. |
| 2012/0059042 | A1 | 3/2012 | Platenburg et al. |
| 2012/0087869 | A1 | 4/2012 | Thakker et al. |
| 2012/0149757 | A1 | 6/2012 | Krainer et al. |
| 2012/0165394 | A1 | 6/2012 | Singh et al. |
| 2012/0190728 | A1 | 7/2012 | Bennett et al. |
| 2013/0109091 | A1 | 5/2013 | Baker et al. |
| 2013/0289092 | A1 | 10/2013 | Rigo et al. |
| 2014/0343127 | A1 | 11/2014 | Kammler |
| 2014/0367278 | A1 | 12/2014 | Zaworski et al. |
| 2016/0068845 | A1 | 3/2016 | Isis et al. |
| 2016/0074474 | A1 | 3/2016 | Passini et al. |
| 2017/0015995 | A1 | 1/2017 | Bennett et al. |
| 2017/0044538 | A1 | 2/2017 | Rigo et al. |
| 2017/0088835 | A1 | 3/2017 | Baker et al. |
| 2017/0363643 | A1 | 12/2017 | Rigo et al. |
| 2018/0273954 | A1 | 9/2018 | Linsley et al. |
| 2018/0291376 | A1 | 10/2018 | Baker et al. |
| 2019/0030058 | A1 | 1/2019 | Bennett et al. |
| 2019/0040384 | A1 | 2/2019 | Bennett et al. |
| 2019/0211330 | A1 | 7/2019 | Hua et al. |

FOREIGN PATENT DOCUMENTS

| | | |
|---|---|---|
| WO | WO 1995/022980 | 8/1995 |
| WO | WO 2001/009311 | 2/2001 |
| WO | WO 2002/038738 | 5/2002 |
| WO | WO 2003/037909 | 5/2003 |
| WO | WO 2004/113867 | 12/2004 |
| WO | WO 2007/002390 | 1/2007 |
| WO | WO 2009/068689 | 6/2009 |
| WO | WO 2009/120700 | 10/2009 |
| WO | WO 2010/091308 | 8/2010 |
| WO | WO 2010/123594 | 10/2010 |
| WO | WO 2010/148249 | 12/2010 |
| WO | WO 2011/032109 | 3/2011 |
| WO | WO 2011/159836 | 12/2011 |
| WO | WO 2012/178146 | 12/2012 |
| WO | WO 2013/009703 | 1/2013 |
| WO | WO 2013/068441 | 5/2013 |
| WO | WO 2013/119916 | 8/2013 |
| WO | WO 2013/173638 | 11/2013 |
| WO | WO 2014/110291 | 7/2014 |
| WO | WO 2015/023941 | 2/2015 |
| WO | WO 2015/051283 | 4/2015 |
| WO | WO 2015/161170 | 10/2015 |
| WO | WO 2016/040748 | 3/2016 |
| WO | WO 2016/164896 | 10/2016 |
| WO | WO 2017/053995 | 3/2017 |
| WO | 2019084050 A1 | 5/2019 |

OTHER PUBLICATIONS

Sloop et al. "Hepatic and glucagon-like peptide-1-mediated reversal of diabetes by glucagon receptor antisense oligonucleotide inhibitors" J Clinical Invest (2004) 113: 1571-1581.
Wilcox et al. "Immobilization and Utilization of the Recombinant Fusion Proteins Trypsin-Streptavidin and Streptavidin-Transglutaminase for Modification of Whey Protein Isolate Functionality" J Agricult Food Chem (2002) 50: 3723-3730.
D'Ydewalle et al., "The Antisense Transcript SMN-AS1 Regulates SMN Expression and Is a Novel Therapeutic Target for Spinal Muscular Atrophy" Neuron (2017) 93: 66-79.
Kramer et al., "Raise the Roof: Boosting the Efficacy of a Spinal Muscular Atrophy Therapy" Neuron (2017) 93: 3-5.
Woo et al., "Gene activation of SMN by selective disruption of lncRNA-mediated recruitment of PRC2 for the treatment of spinal muscular atrophy" Proc Natl Acad Sci USA (2017) 114: E1509-E1518.
Partial Search Report for EP 17814164.4 dated Jan. 23, 2020.
Ramos et al., "Age-dependent SMN expression in disease-relevant tissue and implications for SMA treatment", J Clin Invest (2019) 129: 4817-4831.
Sheng et al., "Comparison of the efficacy of MOE and PMO modifications of systemic antisense oligonucleotides in a severe SMA mouse model", Nucleic Acids Res (2020) 48: 2853-2865.
Zhou et al., "Targeting RNA-splicing for SMA Treatment" Molecules and Cells (2012) 33: 223-228.
Extended Search Report for EP 17814164.4 dated Jun. 5, 2020.
Avila et al., "Trichostatin A increases SMN expression and survival in a mouse model of spinal muscular atrophy" J. Clin. Inves. (2007) 117(3): 659-671.
Batrakova et al., "Mechanism of Pluronic Effect on P-Glycoprotein Efflux System in Blood-Brain Barrier: Contributions of Energy Depletion and Membrane Fluidization" The Journal of Pharmacology and Experimental Therapeutics (2001) 299(2):483-493.
Baughan et al., "Delivery of bifunctional RNAs tha target an intronic repressor and increase SMN levels in an animal model of spinal muscular atrophy" Human Molecular Genetics (2009) 18(9):1600-1611.
Bosch-Marce et al., "Increased IGF-1 in muscle modulates the phenotype of severe SMA mice," Human Molecular Genetics (2011) 20: 1844-1853.
Branch et al., "A good antisense molecule is hard to find," TIBS (1998) 23:45-50.
Brichta et al., "Valproic acid increases the SMN2 protein level: a well-known drug as a potential therapy for spinal muscular atrophy" Human Molecular Genetics (2003) 12(19):2481-2489.
Cartegni et al., "Correction of disease-associated exon skipping by synthetic exon-specific activators" Nat. Struct. Biol. (2003) 10:120-125.
Cartegni et al., "Disruption of an SF2/ASF-dependent exonic splicing enhancer in SMN2 causes spinal muscular atrophy in the absence of SMN1", Nat. Genet., (2002) 30:377-384.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Coady et al., "Development of a single vector system that enhances trans-splicing of SMN2 transcripts." PLoS ONE (2008) 3(10):e3468.
Crooke et al., "Basic Principles of Antisense Therapeutics" Antisense Research and Application (1998) Chapter 1:1-50.
Crooke, "Antisense strategies" Curr. Mol. Med. (2004) 4(5):465-487.
D'Ydewalle. LncRNA as therapeutic target for SMA [online] Jan. 30, 2015 [retrieved Aug. 11, 2015 by ISA/US].
D'Ydewalle "Possible functions of SMN-associated long non-coding RNAs" Johns Hopkins Medicine Apr. 10, 2014.
D'Ydewalle "The long non-coding RNA SMN-AS1 as therapeutic target for SMA" 2016 FightSMA 25th Anniversary Conference Presentation.
Dokka et al., "Novel non-endocyte delivery of antisense oligonucleotides" Advanced Drug Delivery Reviews (2000) 44:35-49.
Dominski et al., "Restoration of correct splicing in thalassemic pre-mRNA by antisense oligonucleotides" PNAS (1993) 90:8673-8677.
Dunckley et al., "Modification of splicing in the dystrophin gene in cultured mdx muscle cells by antisense oligoribonucleotides" Human Mol. Genetics (1998) 7(7):1083-1090.
Dunckley et al., "Modulation of Splicing in the DMD Gene by Antisense Oligoribonucleotides" Nucleosides & Nucleotides (1997) 16(7-9):1665-1668.
Efimov et al., "Phosphono Peptide Nucleic Acids with a Constrained Hydroxproline-Based Backbone" Nucleosides, Nucleotides & Nucleic Acids (2003) 22(5-8):593-599.
Forte et al., "Small interfering RNAs and Antisense Oligonucleotides for Treatment of Neurological Diseases" Current Drug Targets (2005) 6:21-29.
Friedman et al., "Correction of Aberrant Splicing of the Cystic Fibrosis Transmembrane Conductance Regulator (CFTR) Gene by Antisense Oligonucleotides" J. Biol. Chem. (1999) 274:36193-36199.
Genbank Accession No. BC045789.1.

(56) References Cited

OTHER PUBLICATIONS

Gravrilina et al., "Neuronal SMN expression corrects spinal muscular atrophy in severe SMA mice while muscle-specific SMN expression has no phenotypic effect" Hum Mol Genet (2008) 17(8):1063-1075.
Heasman, "Morpholino Oligos: Making Sense of Antisense?" Developmental Biology (2002) 243:209-214.
Hofmann et al., "Htra2-beta1 stimulates an exonic splicing enhancer and can restor full-length SMN expression to survival motor neuron 2 (SMN2)" PNAS (2000) 97(17);9618-9623.
Hua et al., "Antisense correction of SMN2 splicing in the CNS rescues necrosis in a type III SMA mouse model" Genes Dev. (2010) 24:1634-1644.
Hua et al., "Antisense masking of an hnRNP A1/A2 inronic splicing silencer corrects SMN2 splicing in transgenic mice" American Journal of Human Genetics (2008) 82(4):834-848.
Hua et al., "Enhancement of SMN2 exon 7 inclusion by antisense oligonucleotides targeting the exon" PLOS Biology (2007) 5(4):E73.
Hua et al., "Peripheral SMN restoration is essential for long-term rescue of a severe spinal muscular atrophy mouse model," Nature (2011) 478: 123-126.
Inclan et al., "Review of nine cases of chronic progressive muscular atrophy treated with growth hormone by the endoarterial route" Medicina (1958) 26(2): 347-351.
Ittig et al., "Nuclear antisense effects in cyclophilin A pre-mRNA splicing by oligonucleotides: a comparison of tricyclo-DNA with LNA" Nucleic Acids Research (2004) 32(10:346-353.
Jaeger et al., "Transport of Antisense Across the Blood-Brain Barrier" Methods in Molecular Medicine (2005) vol. 106: Antisense Therapeutics, Second Edition, I. Phillips (Ed.) Humana Press, Inc. Totowa, N.J., Cht. 12:237-251.
Kashima et al., "A negative element in SMN2 exon 7 inhibits splicing in spinal muscular atrophy." Nature Genetics (2003) 34(4):460-463.
Kobayashi et al., "Utility of Survival Motor Neuron ELISA for Spinal Muscular Atrophy Clinical and Preclinical Analyses," PLoS ONE (2011) 6:e24269 pp. 1-15.
Kobayashi et al., "Evaluation of peripheral blood mononuclear cell processing and analysis for Survival Motor Neuron protein" PLoS One (2012) 7(11): e50763.
Kole et al., "RNA modulation, repair and remodeling by splice switching oligonucleotides" Acta Biochimica Polonica (2004) 51(2):373-378.
Kole, "Modification ot pre-mRNA splicing by antisense oligonucleotides" Acta Biochimica Polonica (1997) 44(2):231-238.
Krawczak et al., "The mutational spectrum of single base-pair substitutions in mRNA splice junctions of human genes: causes and consequences." Hum. Genet. (1992) 90:41-54.
Kurreck, "Antisense Technologies Improvement Through Novel Chemical Modifications" European Journal of Biochemistry (2003) 270(8):1628-1644.
Lacerra et al., "Restoration of hemoglobin A synthesis in erythroid cells from peripheral blood of thalassemic patients" PNAS (2000) 97(17):9591-9596.
Le et al., "SMNdelta7, the major product of the centromeric survival motor neuron (SMN2) gene, exends survival in mice with spinal muscular atrophy and associates with full-length SMN" Human Molecular Genetics (2005) 14(6):845-857.
Lefebvre et al., "The Role of the SMN Gene in Proximal Spinal Muscular Atrophy" Hum. Mol. Genet. (1998) 7(10):1531-1536.
Lim et al., "Modulation of Survival Motor Neuron Pre-mRNA Splicing by Inhibition of Alternative 3'Splice Site Pairing" J. Biol. Chem. (2001) 276(48):45476-45483.
Lorson et al., "A single nucleotide in the SMN gene regulates splicing and is responsible for spinal muscular atrophy" PNAS (1999) 96:6307-6311.
Lu et al., "Systemic delivery of antisense oligoribonucleotide restores dystrophin expression in body-wide skeletal muscles" PNAS (2005) 102(1):198-203.
Madocsai et al., "Correction of SMN2 Pre-mRNA Splicing by Antisense U7 Small Nuclear RNAs" Molecular Therapy (2005) 12(6):1013-1022.
Matsuzawa et al., "Age-related volumetric changes of brain gray and white matter in healthy infants and children." Cereb Cortex (2001) 11(4):335-342.
Mattis et al., "Subcutaneous adminstration of TC007 reduces disease severity in an animal model of SMA" BioMed Central Neuroscience (2009) 10: 1-6.
Miyajima et al., "Identification of a Cis-Acting Element for the Regulation of SMN Exon 7 Splicing" J. Biol. Chem. (2002) 277(26):23271-23277.
Miyaso et al., "An Intronic Splicing Enhancer Element in Survival Motor Neuron (SMN) Pre-mRNA" J. Biol. Chem. (2003) 278(18):15825-15831.
New England Biolabs 1998/99 Catalog (cover page and pp. 121 and 284).
Ngo et al., Computaitonal Complexity, Protein Structure Predication and the Levinthal Paradox. The Protein Folding Problem and Tertiary Structure Prediction (1994) 433-440 nad 492-495.
Nguyen et al., "A two-site ELISA can quantify upregulation of SMN protein by drugs for spinal muscular atrophy" Neurology (2008) 71(22): 1757-1763.
Ouagazzal, Abdel-Mouttalib. "Reducing Gene Expression in the Brain via Antisense Methods." Current Protocols in Neuroscience. Hoboken: John Wiley & Sons, 2001. N.Chapter 5.
Passini et al., "Antisense Oligonucleotides Delivered to the Mouse CNS Ameliorate Symptoms of Severe Spinal Muscular Atrophy," Science Translational Medicine (2011) 72: 72ra18-72ra18.
Passini et al., "CNS-targeted gene therapy improves survival and motor function in a mouse model of spinal muscular atrophy" J Clin Invest (2010) 120(4): 1253-64.
Piepers et al., "Quantification of SMN protein in leucocytes from spinal muscular atrophy patients: effects of treatment with valproic acid" J Neurol Neurosurg Psychiatry (2011) 82(8): 850-852.
Rebuffat et al., "Gene delivery by a steroid-peptide nucleic acid conjugate" FASEB J. (2002) 19(11):1426-1428.
Reynolds et al., "Rational siRNA design for RNA interference" Nature Biotechnology (2004) 22(3):326-330.
Riessland et al., "SAHA ameliorates the SMA phenotype in two mouse models for spinal muscular atrophy" Human Molecular Genetics (2010) 19(8): 1492-1506.
Rigo et al., "Pharmacology of a central nervous system delivered 2'-O-methoxyethyl-modified survival of motor neuron splicing oligonucleotide in mice and nonhuman primates" J Pharmacol Exp Ther (2014) 350(1): 46-55.
Sanghvi et al., "Heterocyclic Base Modifications in Nucleic Acids and Their Applications in Antisense Oligonucleotides" Antisense Research and Applications (1993) pp. 273-288.
Sazani et al., "Therapeutic potential of antisense oligonucleotides as modulators of alternative splicing" The Journal of Clinical Investigation (2003) 112(4):481-486.
Schmid et al., "Animal models of spinal muscular atrophy" Journal of Child Neurology (2007) 22(8):1004-1012.
Shukla et al., "Quantitative determination of human interleukin 22 (IL-22) in serum using Singulex-Erenna® technology" J Immunol Methods (2013) 390: 30-34.
Sierakowska et al., "Restoration of β-Globin Gene Expression in Mammalian Cells by Antisense Oligonucleotides That Modify the Aberrant Splicing Patierns of Thalassemic Pre-mRNAs" Nucleosides & Nucleotides (1997) 16(7-9):1173-1182.
Sierakowska et al., "Repair of thalassemic human β-globin mRNA in mammalian cells by antisense oligonucleotides" PNAS (1996) 93:12840-12844.
Singh et al., "A short antisense oligonucleotide masking a unique intronic motif prevents skipping of a critical exon in spinal muscular atrophy" RNA Bio (2009) 6(3):341-350.
Singh et al., "In vivo selection reveals combinatorial controls that define a critical exon in the spinal muscular atrophy genes" RNA (2004) 10:1291-1305.
Singh et al., "An extended inhibitory context causes skipping of exon 7 of SMN2 in spinal muscular atrophy" Biochem. Biophys. Res. Comm. (2004) 315(2):381-388.

(56) References Cited

OTHER PUBLICATIONS

Singh et al., "Splicing of a critical exon of human Survival Motor Neuron is regulated by a unique silencer element located in the last intron" Molecular and Cellular Biology (2006) 26(4):1333-1346.
Skolnick et al., "From genes to protein structure and function: novel applications of computational approaches in the genomic era" Trends in Biotech (2000) 18: 34-39.
Skordis et al., "Bifunctional Antisense Oligonucleotides Provide a Trans-Acting Splicing Enhancer that Stimulated SMN2 Gene Expression in Patient Fibroblasts" PNAS (2003) 100(7):4114-4119.
Smith "Antisense oligonucleotide therapy for neurodegenerative disease" Journal of Clinical Investigation (2006) 116:2290-2296.
Swoboda et al., "0.9 First-in-human phase I study to assess safety, tolerability and dose for intrathecal injection of ISIS-SMNRx in SMA patients," Neuromuscular Disorders (2013) 23: 797-798.
Takeshima et al., "Modulation of in vitro splicing of the upstream intron by modifying an intra-exon sequence which is deleted from the dystrophin gene in dystrophin Kobe." J. Clin. Invest. (1995) 95(2):515-520.
Taylor et al., "Induction of endogenous Bcl-xS through the control of Bcl-x pre-mRNA splicing by antisense oligonucleotides" Nat. Biotechnol. (1999) 17:1097-1100.
Translated abstract from JP 2004-344072.
Todd et al., "Ultrasensitive flow-based immunoassays using single-molecule counting" Clin Chem (2007) 53(11): 1990-1995.
Tokuriki et al., "Stability effects of mutations and protein evolvability" Current Opinion in Structual Biology (2009) 19:596-604.
Tsai et al., "Systemic Administration of a Recombinant AAV1 Vector Encoding IGF-1 Improves Disease Manifestaions in SMA Mice" Molecular Therapy (2014) 22: 1450-1459.
Veldink et al., "SMN genotypes producing less SMN protein increase susceptibility to and severity of sporadic ALS" Neurology (2005) 65(6):820-825.
Vindogradov et al., "Nanogels for Oligonucleotide Delivery to the Brain" Bioconjugate Chem. (2004) 15:50-60.
Wadman, "Antisense rescues babies from killer disease" Science (2016) 354(6318): 1359-1360.
Wahlestedt et al., "Potent and nontoxic antisense oligonucleotides containined locked nucleic acids" PNAS (2000) 97(10):5633-5638.
Wang, "Antisense oligodeoxynucleotides selectively suppress expression of the mutant alpha 2(I) collagen allele in type IV osteogenesis imperfecta fibroblasts. A molecular approach to therapeutics of dominant negative disorders." J. Clin. Invest. (1996) 97(2):448-454.
Wells, J.A. "Additivity of Mutational Effects in Proteins" Biochemistry (1990) 29: 8509-8517.
Wenqiang et al. "Mixed-backbone oligonucleotides as second generation antisense agents with reduced phosphorothioate-related side effects" BioOrganic & Medicinal Chemistry Letters (1998) 8(22): 3269-3274.
Williams et al., "Oligonucleotide-mediated survival of motor neuron protein expression in CNS improves phenotype in a mouse model of Spinal Muscular Atrophy" Journal of Neuroscience (2009) 29(24):7633-7638.
Wilton et al., "Specific removal of the nonsense mutation from the mdx dystrophin mRNA using antisense oligonucleotides" Neuromuscul. Disord (1999) 9:330-338.
Yeo et al., "Variation in sequence and organization of splicing regulatory elements in vertebrate genes." Proc. Natl. Acad. Sci. (2004) 101(44):15700-15705.
Zhang et al., "An in vivo reporter system for measuring increased inclusion of exon 7 in SMN2 mRNA: potential therapy of SMA" Gene Ther (2001) 8(20): 1532-1538.
European Search Report for application EP 17151519.0 dated Jul. 18, 2017.
European Search Report for application EP 2943225 dated Jun. 10, 2016.
European Search Report for application EP 06773838 dated Aug. 11, 2010.
European Search Report for application EP 10790221 dated Sep. 4, 2013.
International Search Report for application PCT/US06/24469 dated Sep. 13, 2007.
International Search Report for application PCT/US10/30940 dated Jul. 13, 2010.
International Search Report for application PCT/US2010/39077 dated Aug. 17, 2010.
International Search Report for application PCT/US2015/026326 dated Nov. 3, 2015.
International Search Report for application PCT/US2016/026928 dated Sep. 27, 2016.
International Search Report for application PCT/US2017/037862 dated Oct. 20, 2017.
International Search Report for application PCT/US2017/042463 dated Nov. 27, 2017.
Bennett et al., "Anitsense Oligonucleotides as a tool for gene functionalization and target validation" Biochimica et Biophysics Acta (1999) 1489: 19-30.
Briese et al., "SMN, the product of the spinal muscular atrophy-determining gene, is expressed widely but selectively in the developing human forebrain" J Comp Neurol (2006) 497: 808-816.
Haynes et al., "Proteme Analysis: Biological Assay or Data Archive" Electrophoresis (1998) 19: 1862-1871.
International Search Report and Written Opinion for PCT/US21/019934 dated Aug. 13, 2021, 12 pages.
Kempf et al., "The transforming growth factor-B superfamily member growth differentiation factor-15 protects the heart from ischemia/reperfusion injury" Circulation Research (2006) 98: 351-360.
Mattis et al., "Detection of human survival motor neuron (SMN) protein in mice containing the SMN2 transgene: applicability to preclinical therapy development for spinal muscular atrophy" J Neurosci Methods (2008) 175: 36-43.

COMBINATIONS FOR THE MODULATION OF SMN EXPRESSION

STATEMENT OF GOVERNMENT SUPPORT

This invention was made with Government support under R01 NS096770 awarded by National Institutes of Health. The Government has certain rights in the invention.

SEQUENCE LISTING

The present application is being filed along with a Sequence Listing in electronic format. The Sequence Listing is provided as a file entitled BIOL0293USASEQ_ST25.txt created Dec. 3, 2018 which is approximately 60 Kb. The information in the electronic format of the sequence listing is incorporated herein by reference in its entirety.

FIELD

Certain embodiments are directed to methods and compounds for modulating expression of SMN by inhibiting expression of SMN-NAT and also by altering splicing of SMN. SMN-NAT is the endogenous antisense transcript of Survival of Motor Neuron (SMN). Such methods and compounds are useful for increasing expression of SMN containing exon 7 in cells and animals.

BACKGROUND

Proximal spinal muscular atrophy (SMA) is a genetic, neurodegenerative disorder characterized by the loss of spinal motor neurons. SMA is an autosomal recessive disease of early onset and is currently the leading genetic cause of death among infants. The severity of SMA varies among patients and has thus been classified into three types. Type I SMA is the most severe form with onset at birth or within 6 months and typically results in death within 2 years. Children with type I SMA are unable to sit or walk. Type II SMA is the intermediate form and patients are able to sit, but cannot stand or walk. Patients with type III SMA, a chronic form of the disease, typically develop SMA after 18 months of age (Lefebvre et al., Hum. Mol. Genet., 1998, 7, 1531-1536).

The molecular basis of SMA is caused by the loss of both copies of survival motor neuron gene 1 (SMN1), which may also be known as SMN Telomeric, a protein that is part of a multi-protein complex thought to be involved in snRNP biogenesis and recycling. A nearly identical gene, SMN2, which may also be known as SMN Centromeric, exists in a duplicated region on chromosome 5q13 and modulates disease severity. Expression of the normal SMN1 gene results solely in expression of survival motor neuron (SMN) protein. Although SMN1 and SMN2 have the potential to code for the same protein, SMN2 contains a translationally silent mutation at position +6 of exon 7, which results in inefficient inclusion of exon 7 in SMN2 transcripts. Thus, the predominant form of SMN2 is a truncated version, lacking exon 7, which is unstable and inactive (Cartegni and Krainer, Nat. Genet., 2002, 30, 377-384). Expression of the SMN2 gene results in approximately 10-20% of the SMN protein and 80-90% of the unstable/non-functional SMN-delta7 protein. SMN protein plays a well-established role in assembly of the spliceosome and may also mediate mRNA trafficking in the axon and nerve terminus of neurons.

Antisense technology is an effective means for modulating the expression of one or more specific gene products, including alternative splice products, and is uniquely useful in a number of therapeutic, diagnostic, and research applications. The principle behind antisense technology is that an antisense compound, which hybridizes to a target nucleic acid, modulates gene expression activities such as transcription, splicing or translation through one of a number of anti sense mechanisms. The sequence specificity of antisense compounds makes them extremely attractive as tools for target validation and gene functionalization, as well as therapeutics to selectively modulate the expression of genes involved in disease.

SUMMARY

SMA is a genetic disorder characterized by degeneration of spinal motor neurons. SMA is caused by the homozygous loss of both functional copies of the SMN1 gene. However, the SMN2 gene has the potential to code for the same protein as SMN1 and thus overcome the genetic defect of SMA patients. SMN2 contains a translationally silent mutation (C→T) at position +6 of exon 7, which results in inefficient inclusion of exon 7 in SMN2 transcripts. Therefore, the predominant form of SMN2, one which lacks exon 7, is unstable and inactive. Thus, therapeutic compounds capable of increasing the amount of SMN2 or modulating SMN2 splicing such that the amount of SMN2 transcripts containing exon 7 is increased, would be useful for the treatment of SMA.

Several embodiments provided herein relate to the discovery that antisense compounds targeting SMN-NAT increase expression of SMN2 and that other antisense compounds targeting SMN2 modulate splicing of SMN. Therefore, endogenous levels of SMN2 may be increased by antisense compounds targeted to SMN-NAT. The increased levels of endogenous SMN2 may then be targeted with a separate antisense compound designed to alter the splicing of SMN2 to increase expression of SMN2 containing exon 7. In certain embodiments, treatment of a subject with the combination of a first antisense compound targeted to SMN-NAT and a second antisense compound targeted to SMN2, increases the levels of SMN2 containing exon 7 relative to a subject who only receives a first antisense compound targeted to SMN-NAT or who only receives a second antisense compound targeted to SMN2.

Several embodiments are drawn to methods and compounds for inducing expression of SMN using antisense compounds targeting SMN-NAT and modulating the splicing of SMN to increase expression of SMN containing exon 7.

The present disclosure provides the following non-limiting numbered embodiments:

Embodiment 1: A method of increasing expression of full length SMN2 mRNA in a cell comprising, contacting the cell with a first antisense compound targeted to SMN-NAT and a second antisense compound targeted to SMN.

Embodiment 2: The method of embodiment 1, wherein SMN-NAT comprises a nucleic acid sequence at least 85% identical to SEQ ID NO: 1.

Embodiment 3: The method of embodiment 1, wherein SMN-NAT comprises a nucleic acid sequence at least 90% identical to SEQ ID NO: 1.

Embodiment 4: The method of embodiment 1, wherein SMN-NAT comprises a nucleic acid sequence at least 95% identical to SEQ ID NO: 1.

Embodiment 5: The method of embodiment 1, wherein SMN-NAT comprises a nucleic acid sequence 100% identical to SEQ ID NO: 1.

Embodiment 6: The method of any one of embodiments 1-5, wherein the first antisense compound comprises an oligonucleotide consisting of 12 to 30 linked nucleosides, and wherein the oligonucleotide is at least 85% complementary to a SMN-NAT nucleic acid sequence.

Embodiment 7: The method of embodiment 6, wherein the oligonucleotide is at least 90% complementary over its entire length to an equal length region of a SMN-NAT nucleic acid sequence.

Embodiment 8: The method of embodiment 6, wherein the oligonucleotide is at least 95% complementary over its entire length to an equal length region of a SMN-NAT nucleic acid sequence.

Embodiment 9: The method of embodiment 6, wherein the oligonucleotide is 100% complementary over its entire length to an equal length region of a SMN-NAT nucleic acid sequence.

Embodiment 10: The method of any one of embodiments 1-9, wherein the antisense compound or oligonucleotide complementary to a SMN-NAT nucleic acid sequence is a single-stranded oligonucleotide.

Embodiment 11: The method of any one of embodiments 6-10, wherein the oligonucleotide complementary to a SMN-NAT nucleic acid sequence is a modified oligonucleotide complementary to a SMN-NAT nucleic acid sequence.

Embodiment 12: The method of embodiment 11, wherein the modified oligonucleotide complementary to a SMN-NAT nucleic acid sequence consists of 12 to 30 linked nucleosides and has a nucleobase sequence comprising at least 8 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 13: The method of embodiment 11, wherein the modified oligonucleotide complementary to a SMN-NAT nucleic acid sequence consists of 12 to 30 linked nucleosides and has a nucleobase sequence comprising at least 10 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 14: The method of embodiment 11, wherein the modified oligonucleotide complementary to a SMN-NAT nucleic acid sequence consists of 12 to 30 linked nucleosides and has a nucleobase sequence comprising at least 12 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 15: The method of embodiment 11, wherein the modified oligonucleotide complementary to a SMN-NAT nucleic acid sequence consists of 14 to 30 linked nucleosides and has a nucleobase sequence comprising at least 14 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 16: The method of embodiment 11, wherein the modified oligonucleotide complementary to a SMN-NAT nucleic acid sequence consists of 15 to 30 linked nucleosides and has a nucleobase sequence comprising at least 15 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 17: The method of embodiment 11, wherein the modified oligonucleotide complementary to a SMN-NAT nucleic acid sequence consists of 16 to 30 linked nucleosides and has a nucleobase sequence comprising at least 16 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 18: The method of embodiment 11, wherein the modified oligonucleotide complementary to a SMN-NAT nucleic acid sequence consists of 17 to 30 linked nucleosides and has a nucleobase sequence comprising at least 17 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 19: The method of embodiment 11, wherein the modified oligonucleotide complementary to a SMN-NAT nucleic acid sequence consists of 18 to 30 linked nucleosides and has a nucleobase sequence comprising at least 18 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 20: The method of embodiment 11, wherein the modified oligonucleotide complementary to a SMN-NAT nucleic acid sequence has a nucleobase sequence consisting of the sequence recited in SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 21: The method of any of embodiments 11 to 20, wherein the modified oligonucleotide complementary to a SMN-NAT nucleic acid sequence is a gapmer.

Embodiment 22: The method of any of embodiments 11 to 20, wherein the modified oligonucleotide complementary to a SMN-NAT nucleic acid sequence consists of 20 linked nucleosides having a nucleobase sequence consisting of the sequence recited in SEQ ID NO: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77, wherein the modified oligonucleotide complementary to a SMN-NAT nucleic acid sequence comprises:

a gap segment consisting of linked deoxynucleosides;

a 5' wing segment consisting of linked nucleosides; and a 3' wing segment consisting of linked nucleosides;

wherein the gap segment is positioned between the 5' wing segment and the 3' wing segment and wherein each nucleoside of each wing segment comprises a modified sugar.

Embodiment 23: The method of any of embodiments 11 to 20, wherein the modified oligonucleotide complementary to a SMN-NAT nucleic acid sequence consists of 20 linked nucleosides having a nucleobase sequence consisting of the sequence recited in SEQ ID NO: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77, wherein the modified oligonucleotide complementary to a SMN-NAT nucleic acid sequence comprises:

a gap segment consisting of ten linked deoxynucleosides;

a 5' wing segment consisting of five linked nucleosides; and a 3' wing segment consisting of five linked nucleosides;

wherein the gap segment is positioned between the 5' wing segment and the 3' wing segment, wherein each nucleoside of each wing segment comprises a 2'-O- methoxyethyl sugar; wherein each internucleoside linkage is a phosphorothioate linkage and wherein each cytosine is a 5-methylcytosine.

Embodiment 24: The method of any of embodiments 6-23, wherein the modified oligonucleotide complementary to a SMN-NAT nucleic acid sequence comprises at least one modified internucleoside linkage.

Embodiment 25: The method of embodiment 24, wherein the modified internucleoside linkage is a phosphorothioate internucleoside linkage.

Embodiment 26: The method of any of embodiments 6-23, wherein each internucleoside linkage of the modified oligonucleotide complementary to a SMN-NAT nucleic acid sequence is a modified internucleoside linkage.

Embodiment 27: The method of embodiment 26, wherein the modified internucleoside linkage of the modified oligonucleotide complementary to a SMN-NAT nucleic acid sequence is a phosphorothioate internucleoside linkage.

Embodiment 28: The method of any of embodiments 6-23, wherein each internucleoside linkage of the modified oligonucleotide complementary to a SMN-NAT nucleic acid sequence is either a phosphorothioate internucleoside linkage or a phosphodiester internucleoside linkage.

Embodiment 29: The method of embodiment 28, wherein the modified oligonucleotide complementary to a SMN-NAT nucleic acid sequence has 3 phosphodiester bonds.

Embodiment 30: The method of embodiment 28, wherein the modified oligonucleotide complementary to a SMN-NAT nucleic acid sequence has 4 phosphodiester bonds.

Embodiment 31: The method of embodiment 28, wherein the modified oligonucleotide complementary to a SMN-NAT nucleic acid sequence has 5 phosphodiester bonds.

Embodiment 32: The method of embodiment 28, wherein the modified oligonucleotide complementary to a SMN-NAT nucleic acid sequence has 6 phosphodiester bonds.

Embodiment 33: The method of embodiment 28, wherein the modified oligonucleotide complementary to a SMN-NAT nucleic acid sequence has 2, 3, 4, 5, 6, 7, 8, or 9 phosphodiester bonds.

Embodiment 34: The method of any one of embodiments 11-33, wherein at least one nucleoside comprises a modified sugar.

Embodiment 35: The method of embodiment 34, wherein the modified sugar is a bicyclic sugar comprising a bridge between the 4' and the 2' positions of the sugar.

Embodiment 36: The method of embodiment 35, wherein the bridge is selected from 4'-$CH(CH_3)$—O-2', 4'-$CH_2$-2', 4'-$(CH_2)_2$-2', 4'-$CH_2$—O-2', 4'-$(CH_2)_2$—O-2', 4'-$CH_2$—O—$N(R_1)$-2' and 4'-CH2—$N(R_1)$—O-2'- wherein each R1 is, independently, H, a protecting group or C1-C12 alkyl.

Embodiment 37: The method of embodiment 36, wherein the bridge is 4'-$CH(CH_3)$—O-2'.

Embodiment 38: The method of embodiment 36, wherein the bridge is selected from 4'-$CH_2$—O-2' and 4'-$(CH_2)_2$—O-2'.

Embodiment 39: The method of embodiment 34, wherein the modified sugar comprises a 2'-O-methoxyethyl group.

Embodiment 40: The method of any one of embodiments 11-33, wherein at least one nucleoside comprises a modified nucleobase.

Embodiment 41: The method of any one of embodiments 11-39, wherein the oligonucleotide complementary to a SMN-NAT nucleic acid sequence comprises a 5-methylcytosine.

Embodiment 42: The method of any one of embodiments 1-41, wherein contacting the cell with the first antisense compound or modified oligonucleotide complementary to a SMN-NAT nucleic acid sequence increases expression of SMN by at least 20%.

Embodiment 43: The method of any one of embodiments 1-41, wherein contacting the cell with the first antisense compound or modified oligonucleotide complementary to a SMN-NAT nucleic acid sequence increases expression of SMN by at least 30%.

Embodiment 44: The method of any one of embodiments 1-41, wherein contacting the cell with the first antisense compound or modified oligonucleotide complementary to a SMN-NAT nucleic acid sequence increases expression of SMN by at least 40%.

Embodiment 45: The method of any one of embodiments 1-41, wherein contacting the cell with the first antisense compound or modified oligonucleotide complementary to a SMN-NAT nucleic acid sequence increases expression of SMN by at least 50%.

Embodiment 46: The method of any one of embodiments 1-41, wherein contacting the cell with the first antisense compound or modified oligonucleotide complementary to a SMN-NAT nucleic acid sequence increases expression of SMN by at least 60%.

Embodiment 47: The method of any one of embodiments 1-41, wherein contacting the cell with the first antisense compound or modified oligonucleotide complementary to a SMN-NAT nucleic acid sequence increases expression of SMN by at least 70%.

Embodiment 48: The method of any one of embodiments 1-41, wherein contacting the cell with the first antisense compound or modified oligonucleotide complementary to a SMN-NAT nucleic acid sequence increases expression of SMN by at least 80%.

Embodiment 49: The method of any one of embodiments 1-41, wherein contacting the cell with the first antisense compound or modified oligonucleotide complementary to a SMN-NAT nucleic acid sequence increases expression of SMN by at least 90%.

Embodiment 50: The method of any one of embodiments 1-41, wherein contacting the cell with the first antisense compound or modified oligonucleotide complementary to a SMN-NAT nucleic acid sequence increases expression of SMN by at least 100%.

Embodiment 51: The method of any one of embodiments 1-41, wherein contacting the cell with the first antisense compound or modified oligonucleotide complementary to a SMN-NAT nucleic acid sequence increases expression of SMN by at least 110%.

Embodiment 52: The method of any one of embodiments 1-41, wherein contacting the cell with the first antisense compound or modified oligonucleotide complementary to a SMN-NAT nucleic acid sequence increases expression of SMN by at least 120%.

Embodiment 53: The method of any one of embodiments 1-41, wherein the first antisense compound is ISIS 813208.

Embodiment 54: The method of any one of embodiments 1-53, wherein the second antisense compound comprises an oligonucleotide consisting of 12 to 30 linked nucleosides, and wherein the oligonucleotide is at least 85% complementary to an SMN nucleic acid sequence.

Embodiment 55: The method of embodiment 54, wherein the second antisense compound or oligonucleotide complementary to an SMN nucleic acid sequence is a single-stranded oligonucleotide.

Embodiment 56: The method of any one of embodiments 54 or 55, wherein the oligonucleotide complementary to an SMN nucleic acid sequence is a modified oligonucleotide complementary to an SMN nucleic acid sequence.

Embodiment 57: The method of embodiment 56, wherein the modified oligonucleotide complementary to an SMN nucleic acid sequence consists of 12 to 30 linked nucleosides and has a nucleobase sequence comprising at least 8 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 58: The method of embodiment 56, wherein the modified oligonucleotide complementary to an SMN nucleic acid sequence consists of 12 to 30 linked nucleosides and has a nucleobase sequence comprising at least 10 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 59: The method of embodiment 56, wherein the modified oligonucleotide complementary to an SMN nucleic acid sequence consists of 12 to 30 linked nucleosides and has a nucleobase sequence comprising at least 12 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 60: The method of embodiment 56, wherein the modified oligonucleotide complementary to an SMN nucleic acid sequence consists of 14 to 30 linked nucleosides and has a nucleobase sequence comprising at least 14 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 61: The method of embodiment 56, wherein the modified oligonucleotide complementary to an SMN nucleic acid sequence consists of 15 to 30 linked nucleosides and has a nucleobase sequence comprising at least 15 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 62: The method of embodiment 56, wherein the modified oligonucleotide complementary to an SMN nucleic acid sequence consists of 16 to 30 linked nucleosides and has a nucleobase sequence comprising at least 16 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 63: The method of embodiment 56, wherein the modified oligonucleotide complementary to an SMN nucleic acid sequence consists of 17 to 30 linked nucleosides and has a nucleobase sequence comprising at least 17 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 64: The method of embodiment 56, wherein the modified oligonucleotide complementary to an SMN nucleic acid sequence consists of 18 to 30 linked nucleosides and has a nucleobase sequence comprising at least 18 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 65: The method of embodiment 56, wherein the modified oligonucleotide complementary to an SMN nucleic acid sequence has a nucleobase sequence consisting of the sequence recited in SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 66: The method of any of embodiments 54-65, wherein the modified oligonucleotide complementary to an SMN nucleic acid sequence comprises at least one modified internucleoside linkage.

Embodiment 67: The method of embodiment 66, wherein the modified internucleoside linkage is a phosphorothioate internucleoside linkage.

Embodiment 68: The method of any of embodiments 53-64, wherein each internucleoside linkage of the modified oligonucleotide complementary to an SMN nucleic acid sequence is a modified internucleoside linkage.

Embodiment 69: The method of embodiment 67, wherein the modified internucleoside linkage is a phosphorothioate internucleoside linkage.

Embodiment 70: The method of any of embodiments 54-65, wherein each internucleoside linkage of the modified oligonucleotide complementary to an SMN nucleic acid sequence is either a phosphodiester internucleoside linkage or a phosphorothioate internucleoside linkage.

Embodiment 71: The method of embodiment 70, wherein the modified oligonucleotide complementary to an SMN nucleic acid sequence has 6 phospodiester internucleoside linkages.

Embodiment 72: The method of embodiment 70, wherein the modified oligonucleotide complementary to an SMN nucleic acid sequence has 8 phospodiester internucleoside linkages.

Embodiment 73: The method of embodiment 70, wherein the modified oligonucleotide complementary to an SMN nucleic acid sequence has 13 phospodiester internucleoside linkages.

Embodiment 74: The method of embodiment 70, wherein the modified oligonucleotide complementary to an SMN nucleic acid sequence has 4, 5, 6, 7, 8, 9, 10, 11, 12, 13, 14, 15, or 16 phospodiester internucleoside linkages.

Embodiment 75: The method of any one of embodiments 54-74, wherein at least one nucleoside comprises a modified sugar.

Embodiment 76: The method of any one of embodiments 54-74, wherein each nucleoside comprises a modified sugar.

Embodiment 77: The method of embodiment 75 or 76, wherein the modified sugar is a bicyclic sugar comprising a bridge between the 4' and the 2' positions of the sugar.

Embodiment 78: The method of embodiment 77, wherein the bridge is selected from 4'-$CH(CH_3)$—O-2', 4'-$CH_2$-2', 4'-$(CH_2)_2$-2', 4'-$CH_2$—O-2', 4'-$(CH_2)_2$—O-2', 4'-$CH_2$—O—$N(R_1)$-2' and 4'-CH2—$N(R_1)$—O-2'- wherein each R1 is, independently, H, a protecting group or C1-C12 alkyl.

Embodiment 79: The method of embodiment 77, wherein the bridge is 4'-$CH(CH_3)$—O-2'.

Embodiment 80: The method of embodiment 77, wherein the bridge is selected from 4'-$CH_2$—O-2' and 4'-$(CH_2)_2$—O-2'.

Embodiment 81: The method of embodiment 75 or 76, wherein the modified sugar comprises a 2'-O-methoxyethyl group.

Embodiment 82: The method of embodiment 75 or 76, wherein the modified sugar comprises a 2'-O-methyl group.

Embodiment 83: The method of any one of embodiments 54-82, wherein at least one nucleoside comprises a modified nucleobase.

Embodiment 84: The method of any one of embodiments 54-82, wherein each cytosine is a 5-methylcytosine.

Embodiment 85: The method of any one of embodiments 54-82, wherein the oligonucleotide comprises a 5-methylcytosine.

Embodiment 86: The method of any one of embodiments 1-85, wherein the second antisense compound is ISIS 449323.

Embodiment 87: The method of any of embodiments 1-86, wherein the cell is in a subject.

Embodiment 88: The method of embodiment 87, wherein the subject is a human.

Embodiment 89: The method of embodiment 87, wherein the subject has type I SMA.

Embodiment 90: The method of embodiment 87, wherein the subject has type II SMA.

Embodiment 91: The method of embodiment 87, wherein the subject has type III SMA.

Embodiment 92: The method of embodiment 87, wherein the subject has type IV SMA.

Embodiment 93: The method of any of embodiments 86 to 92, wherein the subject has one or more indicators of SMA.

Embodiment 94: The method of any of embodiments 86 to 93, wherein the subject has one or more symptoms of SMA.

Embodiment 95: A composition comprising a first antisense compound targeted to SMN-NAT, a second antisense compound targeted to SMN, and a pharmaceutically acceptable carrier or diluent.

Embodiment 96: The composition of embodiment 95, wherein SMN-NAT comprises a nucleic acid sequence at least 85% identical to SEQ ID NO: 1.

Embodiment 97: The composition of embodiment 95, wherein SMN-NAT comprises a nucleic acid sequence at least 90% identical to SEQ ID NO: 1.

Embodiment 98: The composition of embodiment 95, wherein SMN-NAT comprises a nucleic acid sequence at least 95% identical to SEQ ID NO: 1.

Embodiment 99: The composition of embodiment 95, wherein SMN-NAT comprises a nucleic acid sequence 100% identical to SEQ ID NO: 1.

Embodiment 100: The composition of any one of embodiments 95-99, wherein the first antisense compound comprises an oligonucleotide consisting of 12 to 30 linked nucleosides, and wherein the oligonucleotide is at least 85% complementary to a SMN-NAT nucleic acid sequence.

Embodiment 101: The composition of embodiment 100, wherein the oligonucleotide is at least 90% complementary over its entire length to an equal length region of a SMN-NAT nucleic acid sequence.

Embodiment 102: The composition of embodiment 100, wherein the oligonucleotide is at least 95% complementary over its entire length to an equal length region of a SMN-NAT nucleic acid sequence.

Embodiment 103: The composition of embodiment 100, wherein the oligonucleotide is 100% complementary over its entire length to an equal length region of a SMN-NAT nucleic acid sequence.

Embodiment 104: The composition of any one of embodiments 95-103, wherein the antisense compound or oligonucleotide complementary to a SMN-NAT nucleic acid sequence is a single-stranded oligonucleotide.

Embodiment 105: The composition of any one of embodiments 100-104, wherein the oligonucleotide complementary to a SMN-NAT nucleic acid sequence is a modified oligonucleotide complementary to a SMN-NAT nucleic acid sequence.

Embodiment 106: The composition of embodiment 105, wherein the modified oligonucleotide complementary to a SMN-NAT nucleic acid sequence consists of 12 to 30 linked nucleosides and has a nucleobase sequence comprising at least 8 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 107: The composition of embodiment 105, wherein the modified oligonucleotide complementary to a SMN-NAT nucleic acid sequence consists of 12 to 30 linked nucleosides and has a nucleobase sequence comprising at least 10 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 108: The composition of embodiment 105, wherein the modified oligonucleotide complementary to a SMN-NAT nucleic acid sequence consists of 12 to 30 linked nucleosides and has a nucleobase sequence comprising at least 12 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 109: The composition of embodiment 105, wherein the modified oligonucleotide complementary to a SMN-NAT nucleic acid sequence consists of 14 to 30 linked nucleosides and has a nucleobase sequence comprising at least 14 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 110: The composition of embodiment 105, wherein the modified oligonucleotide complementary to a SMN-NAT nucleic acid sequence consists of 15 to 30 linked nucleosides and has a nucleobase sequence comprising at least 15 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 111: The composition of embodiment 105, wherein the modified oligonucleotide complementary to a SMN-NAT nucleic acid sequence consists of 16 to 30 linked nucleosides and has a nucleobase sequence comprising at least 16 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 112: The composition of embodiment 105, wherein the modified oligonucleotide complementary to a SMN-NAT nucleic acid sequence consists of 17 to 30 linked nucleosides and has a nucleobase sequence comprising at least 17 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 113: The composition of embodiment 105, wherein the modified oligonucleotide complementary to a SMN-NAT nucleic acid sequence consists of 18 to 30 linked nucleosides and has a nucleobase sequence comprising at least 18 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 114: The composition of embodiment 105, wherein the modified oligonucleotide complementary to a SMN-NAT nucleic acid sequence has a nucleobase sequence consisting of the sequence recited in SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

Embodiment 115: The composition of any of embodiments 105 to 114, wherein the modified oligonucleotide complementary to a SMN-NAT nucleic acid sequence is a gapmer.

Embodiment 116: The composition of any of embodiments 105 to 114, wherein the modified oligonucleotide complementary to a SMN-NAT nucleic acid sequence consists of 20 linked nucleosides having a nucleobase sequence consisting of the sequence recited in SEQ ID NO: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77, wherein the modified oligonucleotide complementary to a SMN-NAT nucleic acid sequence comprises:

a gap segment consisting of linked deoxynucleosides;

a 5' wing segment consisting of linked nucleosides; and a 3' wing segment consisting of linked nucleosides;

wherein the gap segment is positioned between the 5' wing segment and the 3' wing segment and wherein each nucleoside of each wing segment comprises a modified sugar.

Embodiment 117: The composition of any of embodiments 105 to 114, wherein the modified oligonucleotide complementary to a SMN-NAT nucleic acid sequence consists of 20 linked nucleosides having a nucleobase sequence consisting of the sequence recited in SEQ ID NO: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77, wherein the modified oligonucleotide complementary to a SMN-NAT nucleic acid sequence comprises:

a gap segment consisting of ten linked deoxynucleosides;

a 5' wing segment consisting of five linked nucleosides; and a 3' wing segment consisting of five linked nucleosides;

wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage and wherein each cytosine is a 5-methylcytosine.

Embodiment 118: The composition of any of embodiments 100-117, wherein the modified oligonucleotide complementary to a SMN-NAT nucleic acid sequence comprises at least one modified internucleoside linkage.

Embodiment 119: The composition of embodiment 118, wherein the modified internucleoside linkage is a phosphorothioate internucleoside linkage.

Embodiment 120: The composition of any of embodiments 100-117, wherein each internucleoside linkage of the modified oligonucleotide complementary to a SMN-NAT nucleic acid sequence is a modified internucleoside linkage.

Embodiment 121: The composition of embodiment 120, wherein the modified internucleoside linkage of the modified oligonucleotide complementary to a SMN-NAT nucleic acid sequence is a phosphorothioate internucleoside linkage.

Embodiment 122: The composition of any of embodiments 100-117, wherein each internucleoside linkage of the modified oligonucleotide complementary to a SMN-NAT nucleic acid sequence is either a phosphorothioate internucleoside linkage or a phosphodiester internucleoside linkage.

Embodiment 123: The composition of embodiment 122, wherein the modified oligonucleotide complementary to a SMN-NAT nucleic acid sequence has 3 phosphodiester bonds.

Embodiment 124: The composition of embodiment 122, wherein the modified oligonucleotide complementary to a SMN-NAT nucleic acid sequence has 4 phosphodiester bonds.

Embodiment 125: The composition of embodiment 122, wherein the modified oligonucleotide complementary to a SMN-NAT nucleic acid sequence has 5 phosphodiester bonds.

Embodiment 126: The composition of embodiment 122, wherein the modified oligonucleotide complementary to a SMN-NAT nucleic acid sequence has 6 phosphodiester bonds.

Embodiment 127: The composition of embodiment 122, wherein the modified oligonucleotide complementary to a SMN-NAT nucleic acid sequence has 2, 3, 4, 5, 6, 7, 8, or 9 phosphodiester bonds.

Embodiment 128: The composition of any one of embodiments 105-127, wherein at least one nucleoside comprises a modified sugar.

Embodiment 129: The composition of embodiment 128, wherein the modified sugar is a bicyclic sugar comprising a bridge between the 4' and the 2' positions of the sugar.

Embodiment 130: The composition of embodiment 129, wherein the bridge is selected from 4'-$CH(CH_3)$—O-2', 4'-$CH_2$-2', 4'-$(CH_2)_2$-2', 4'-$CH_2$—O-2', 4'-$(CH_2)_2$—O-2', 4'-$CH_2$—O—$N(R_1)$-2' and 4'-CH2—$N(R_1)$—O-2'-wherein each R1 is, independently, H, a protecting group or C1-C12 alkyl.

Embodiment 131: The composition of embodiment 130, wherein the bridge is 4'-$CH(CH_3)$—O-2'.

Embodiment 132: The composition of embodiment 130, wherein the bridge is selected from 4'-$CH_2$—O-2' and 4'-$(CH_2)_2$—O-2'.

Embodiment 133: The composition of embodiment 128, wherein the modified sugar comprises a 2'-O-methoxyethyl group.

Embodiment 134: The composition of any one of embodiments 105-127, wherein at least one nucleoside comprises a modified nucleobase.

Embodiment 135: The composition of any one of embodiments 105-134, wherein the oligonucleotide complementary to a SMN-NAT nucleic acid sequence comprises a 5-methylcytosine.

Embodiment 136: The composition of any one of embodiments 95-135, wherein the first antisense compound is ISIS 813208.

Embodiment 137: The composition of any one of embodiments 95-136, wherein the second antisense compound comprises an oligonucleotide consisting of 12 to 30 linked nucleosides, and wherein the oligonucleotide is at least 85% complementary to an SMN nucleic acid sequence.

Embodiment 138: The composition of embodiment 137, wherein the second antisense compound or oligonucleotide complementary to an SMN nucleic acid sequence is a single-stranded oligonucleotide.

Embodiment 139: The composition of any one of embodiments 137 or 138, wherein the oligonucleotide complementary to an SMN nucleic acid sequence is a modified oligonucleotide complementary to an SMN nucleic acid sequence.

Embodiment 140: The composition of embodiment 139, wherein the modified oligonucleotide complementary to an SMN nucleic acid sequence consists of 12 to 30 linked nucleosides and has a nucleobase sequence comprising at least 8 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 141: The composition of embodiment 139, wherein the modified oligonucleotide complementary to an SMN nucleic acid sequence consists of 12 to 30 linked nucleosides and has a nucleobase sequence comprising at least 10 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 142: The composition of embodiment 139, wherein the modified oligonucleotide complementary to an SMN nucleic acid sequence consists of 12 to 30 linked nucleosides and has a nucleobase sequence comprising at least 12 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 143: The composition of embodiment 139, wherein the modified oligonucleotide complementary to an SMN nucleic acid sequence consists of 14 to 30 linked nucleosides and has a nucleobase sequence comprising at least 14 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 144: The composition of embodiment 139, wherein the modified oligonucleotide complementary to an SMN nucleic acid sequence consists of 15 to 30 linked nucleosides and has a nucleobase sequence comprising at least 15 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 145: The composition of embodiment 139, wherein the modified oligonucleotide complementary to an SMN nucleic acid sequence consists of 16 to 30 linked nucleosides and has a nucleobase sequence comprising at least 16 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 146: The composition of embodiment 139, wherein the modified oligonucleotide complementary to an SMN nucleic acid sequence consists of 17 to 30 linked nucleosides and has a nucleobase sequence comprising at least 17 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 147: The composition of embodiment 139, wherein the modified oligonucleotide complementary to an SMN nucleic acid sequence consists of 18 to 30 linked nucleosides and has a nucleobase sequence comprising at least 18 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 148: The composition of embodiment 139, wherein the modified oligonucleotide complementary to an SMN nucleic acid sequence has a nucleobase sequence consisting of the sequence recited in SEQ ID NOs: 81, 82, 83, 84, 85, 86, 87, 88, 89, 90, 91, 92, 93, 94, 95, 96, 97, 98, 99, 100, 101, 102, 103, or 104.

Embodiment 149: The composition of any of embodiments 137-148, wherein the modified oligonucleotide complementary to an SMN nucleic acid sequence comprises at least one modified internucleoside linkage.

Embodiment 150: The composition of embodiment 149, wherein the modified internucleoside linkage is a phosphorothioate internucleoside linkage.

Embodiment 151: The composition of any of embodiments 137-148, wherein each internucleoside linkage of the modified oligonucleotide complementary to an SMN nucleic acid sequence is a modified internucleoside linkage.

Embodiment 152: The composition of embodiment 151, wherein the modified internucleoside linkage is a phosphorothioate internucleoside linkage.

Embodiment 153: The composition of any of embodiments 137-148, wherein each internucleoside linkage of the modified oligonucleotide complementary to an SMN nucleic acid sequence is either a phosphodiester internucleoside linkage or a phosphorothioate internucleoside linkage.

Embodiment 154: The composition of embodiment 153, wherein the modified oligonucleotide complementary to an SMN nucleic acid sequence has 6 phospodiester internucleoside linkages.

Embodiment 155: The composition of embodiment 153, wherein the modified oligonucleotide complementary to an SMN nucleic acid sequence has 8 phospodiester internucleoside linkages.

Embodiment 156: The composition of embodiment 153, wherein the modified oligonucleotide complementary to an SMN nucleic acid sequence has 13 phospodiester internucleoside linkages.

Embodiment 157: The composition of embodiment 153, wherein the modified oligonucleotide complementary to an SMN nucleic acid sequence has 4, 5, 6, 7, 8, 9, 10, 11, 12, 13, 14, 15, or 16 phospodiester internucleoside linkages.

Embodiment 158: The composition of any one of embodiments 137-157, wherein at least one nucleoside comprises a modified sugar.

Embodiment 159: The composition of any one of embodiments 137-157, wherein each nucleoside comprises a modified sugar.

Embodiment 160: The composition of embodiment 158 or 159, wherein the modified sugar is a bicyclic sugar comprising a bridge between the 4' and the 2' positions of the sugar.

Embodiment 161: The composition of embodiment 160, wherein the bridge is selected from 4'-$CH(CH_3)$—O-2', 4'-$CH_2$-2', 4'-$(CH_2)_2$-2', 4'-$CH_2$—O-2', 4'-$(CH_2)_2$—O-2', 4'-$CH_2$—O—$N(R_1)$-2' and 4'-CH2—$N(R_1)$—O-2'- wherein each R1 is, independently, H, a protecting group or C1-C12 alkyl.

Embodiment 162: The composition of embodiment 160, wherein the bridge is 4'-$CH(CH_3)$—O-2'.

Embodiment 163: The composition of embodiment 160, wherein the bridge is selected from 4'-$CH_2$—O-2' and 4'-$(CH_2)_2$—O-2'.

Embodiment 164: The composition of embodiment 158 or 159, wherein the modified sugar comprises a 2'-O-methoxyethyl group.

Embodiment 165: The composition of embodiment 158 or 159, wherein the modified sugar comprises a 2'-O-methyl group.

Embodiment 166: The composition of any one of embodiments 54-82, wherein at least one nucleoside comprises a modified nucleobase.

Embodiment 167: The composition of any one of embodiments 137-166, wherein each cytosine is a 5-methylcytosine.

Embodiment 168: The composition of any one of embodiments 137-166, wherein the oligonucleotide comprises a 5-methylcytosine.

Embodiment 169: The composition of any one of embodiments 105-168, wherein the second antisense compound is ISIS 449323.

Embodiment 170: The composition of any of embodiments 105-169, for use in therapy.

Embodiment 171: Use of the composition of any of embodiments 105-169 for a preparation of a medicament for the treatment of SMA.

Embodiment 172: A method of treating a subject having SMA, comprising administering the composition of any of embodiments 105-169 to a subject in need thereof.

Embodiment 173: The method of embodiment 172, wherein the subject has type I SMA.

Embodiment 174: The method of embodiment 172, wherein the subject has type II SMA.

Embodiment 175: The method of embodiment 172, wherein the subject has type III SMA.

Embodiment 176: The method of embodiment 172, wherein the subject has type IV SMA.

Embodiment 177: The method of embodiment 172, wherein the subject has one or more indicators of SMA.

Embodiment 178: The method of embodiment 172, wherein the subject has one or more symptoms of SMA.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

It is understood that the sequence set forth in each SEQ ID NO described herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., $21^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "SMN-NAT" means a natural antisense transcript of SMN. In certain embodiments, SMN-NAT transcript comprises GenBank accession #BC045789.1 (SEQ ID NO. 1).

As used herein, "Survival of Motor Neuron" or "SMN" means any SMN nucleic acid or protein. "SMN nucleic acid" means any nucleic acid encoding SMN. For example, in certain embodiments, a SMN nucleic acid includes a DNA sequence encoding SMN, an RNA sequence transcribed from DNA encoding SMN, including a non-protein encoding (i.e. non-coding) RNA sequence, and an mRNA sequence encoding SMN. "SMN mRNA" means an mRNA encoding a SMN protein.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, “furanosyl” means a structure comprising a 5-membered ring comprising four carbon atoms and one oxygen atom.

As used herein, “naturally occurring sugar moiety” means a ribofuranosyl as found in naturally occurring RNA or a deoxyribofuranosyl as found in naturally occurring DNA.

As used herein, “sugar moiety” means a naturally occurring sugar moiety or a modified sugar moiety of a nucleoside.

As used herein, “modified sugar moiety” means a substituted sugar moiety, a bicyclic or tricyclic sugar moiety, or a sugar surrogate.

As used herein, “substituted sugar moiety” means a furanosyl comprising at least one substituent group that differs from that of a naturally occurring sugar moiety. Substituted sugar moieties include, but are not limited to furanosyls comprising substituents at the 2'-position, the 3'-position, the 5'-position and/or the 4'-position. As used herein, “2'-substituted sugar moiety” means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, “MOE” means $-OCH_2CH_2OCH_3$.

As used herein, “bicyclic sugar moiety” means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein the term “sugar surrogate” means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, “nucleotide” means a nucleoside further comprising a phosphate linking group. As used herein, “linked nucleosides” may or may not be linked by phosphate linkages and thus includes, but is not limited to “linked nucleotides.” As used herein, “linked nucleosides” are nucleosides that are connected in a continuous sequence (i.e. no additional nucleosides are present between those that are linked).

As used herein, “nucleobase” means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, “heterocyclic base” or “heterocyclic nucleobase” means a nucleobase comprising a heterocyclic structure.

As used herein the terms, “unmodified nucleobase” or “naturally occurring nucleobase” means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, “modified nucleobase” means any nucleobase that is not a naturally occurring nucleobase.

As used herein, “modified nucleoside” means a nucleoside comprising at least one chemical modification compared to naturally occurring RNA or DNA nucleosides. Modified nucleosides comprise a modified sugar moiety and/or a modified nucleobase.

As used herein, “bicyclic nucleoside” or “BNA” means a nucleoside comprising a bicyclic sugar moiety.

As used herein, “constrained ethyl nucleoside” or “cEt” means a nucleoside comprising a bicyclic sugar moiety comprising a 4'-$CH(CH_3)$—O-2' bridge.

As used herein, “locked nucleic acid nucleoside” or “LNA” means a nucleoside comprising a bicyclic sugar moiety comprising a 4'-$CH_2$—O-2' bridge.

As used herein, “2'-substituted nucleoside” means a nucleoside comprising a substituent at the 2'-position ther than H or OH. Unless otherwise indicated, a 2'-substituted nucleoside is not a bicyclic nucleoside.

As used herein, “2'-deoxynucleoside” means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, “oligonucleotide” means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein “oligonucleoside” means an oligonucleotide in which none of the internucleoside linkages contains a phosphorus atom. As used herein, oligonucleotides include oligonucleosides.

As used herein, “modified oligonucleotide” means an oligonucleotide comprising at least one modified nucleoside and/or at least one modified internucleoside linkage.

As used herein “internucleoside linkage” means a covalent linkage between adjacent nucleosides in an oligonucleotide.

As used herein “naturally occurring internucleoside linkage” means a 3' to 5' phosphodiester linkage.

As used herein, “modified internucleoside linkage” means any internucleoside linkage other than a naturally occurring internucleoside linkage.

As used herein, “oligomeric compound” means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, “terminal group” means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-mRNA includes one or more intron.

As used herein, "transcript" means an RNA molecule transcribed from DNA. Transcripts include, but are not limited to mRNA, pre-mRNA, and partially processed RNA.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl ($-C(O)R_{aa}$), carboxyl ($-C(O)O-R_{aa}$), aliphatic groups, alicyclic groups, alkoxy, substituted oxy ($-O-R_{aa}$), aryl, aralkyl, heterocyclic radical, heteroaryl, heteroarylalkyl, amino ($-N(R_{bb})(R_{cc})$), imino($=NR_{bb}$), amido ($-C(O)N(R_{bb})(R_{cc})$ or $-N(R_{bb})C(O)R_{aa}$), azido ($-N_3$), nitro ($-NO_2$), cyano ($-CN$), carbamido ($-OC(O)N(R_{bb})(R_{cc})$ or $-N(R_{bb})C(O)OR_{aa}$), ureido ($-N(R_{bb})C(O)N(R_{bb})(R_{cc})$), thioureido ($-N(R_{bb})C(S)N(R_{bb})$-$(R_{cc})$), guanidinyl ($-N(R_{bb})C(=NR_{bb})N(R_{bb})(R_{cc})$), amidinyl ($-C(=NR_{bb})N(R_{bb})(R_{cc})$ or $-N(R_{bb})C(=NR_{bb})(R_{aa})$), thiol ($-SR_{bb}$), sulfinyl ($-S(O)R_{bb}$), sulfonyl ($-S(O)_2R_{bb}$) and sulfonamidyl ($-S(O)_2N(R_{bb})(R_{cc})$ or $-N(R_{bb})S-(O)_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond.

An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications one or more nucleoside (including modifications to the sugar moiety and/or the nucleobase) and/or modifications to one or more internucleoside linkage.

Certain Sugar Moieties

In certain embodiments, oligomeric compounds of the invention comprise one or more modifed nucleosides comprising a modifed sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substitued sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-$OCH_3$ ("OMe" or "O-methyl"), and 2'-$O(CH_2)_2OCH_3$ ("MOE"). In certain embodiments, sugar substituents at the 2' position is selected from allyl, amino, azido, thio, O-allyl, O—$C_1$-$C_{10}$ alkyl, O—$C_1$-$C_{10}$ substituted alkyl; O—$C_1$-$C_{10}$ alkoxy; O—$C_1$-$C_{10}$ substituted alkoxy, $OCF_3$, $O(CH_2)_2SCH_3$, $O(CH_2)_2$—O—N(Rm)(Rn), and O—$CH_2$—C(=O)—N(Rm)(Rn), where each Rm and Rn is, independently, H or substituted or unsubstituted $C_1$-$C_{10}$ alkyl. Examples of sugar substituents at the 5'-position, include, but are not limited to; 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5', 2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—$C_1$-$C_{10}$ alkoxy; O—$C_1$-$C_{10}$ substituted alkoxy, SH, CN, OCN, $CF_3$, $OCF_3$, O-alkyl, S-alkyl, N($R_m$)-alkyl; O-alkenyl, S-alkenyl, or N($R_m$)-alkenyl; O-alkynyl, S-alkynyl, N($R_m$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R_m$)($R_n$) or O—$CH_2$—C(═O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH═$CH_2$, O—$CH_2$—CH═$CH_2$, $OCH_2CH_2OCH_3$, $O(CH_2)_2SCH_3$, O—$(CH_2)_2$—O—N($R_m$)($R_n$), $O(CH_2)_2O(CH_2)_2N(CH_3)_2$, and N-substituted acetamide (O—$CH_2$—C(═O)—N($R_m$)($R_n$) where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, $O(CH_2)_2$ $SCH_3$, O—$(CH_2)_2$—O—$N(CH_3)_2$, —$O(CH_2)_2O(CH_2)_2N(CH_3)_2$, and O—$CH_2$—C(═O)—N(H)$CH_3$.

In certain embodiments, a 2'-substituted nucleoside comprises a sugar moiety comprising a 2'-substituent group selected from F, O—$CH_3$, and $OCH_2CH_2OCH_3$.

Certain modifed sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C($R_a$)($R_b$)]$_n$—, —[C($R_a$)($R_b$)]$_n$—O—, —C($R_aR_b$)—N(R)—O— or, —C($R_aR_b$)—O—N(R)—; 4'$CH_2$-2', 4'-$(CH_2)_2$-2', 4'-$(CH_2)_3$-2', 4'-($CH_2$)—O-2' (LNA); 4'-($CH_2$)—S-2'; 4'-$(CH_2)_2$—O-2' (ENA); 4'-CH($CH_3$)—O-2' (cEt) and 4'-CH($CH_2OCH_3$)—O-2', and analogs thereof (see, e.g., U.S. Pat. No. 7,399,845, issued on Jul. 15, 2008); 4'-C($CH_3$)($CH_3$)—O-2' and analogs thereof, (see, e.g., WO2009/006478, published Jan. 8, 2009); 4'-$CH_2$—N($OCH_3$)-2' and analogs thereof (see, e.g., WO2008/150729, published Dec. 11, 2008); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya, et al., *J. Org. Chem.*, 2009, 74, 118-134); and 4'-$CH_2$—C(═$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C($R_a$)($R_b$)]$_n$—, —C($R_a$)═C($R_b$)—, —C($R_a$)═N—, —C(═N$R_a$)—, —C(═O)—, —C(═S)—, —O—, —Si$(R_a)_2$—, —S(═O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(═O)—H), substituted acyl, CN, sulfonyl (S(═O)$_2$-$J_1$), or sulfoxyl (S(═O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(═O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, and (J) propylene carbocyclic (4'-$(CH_2)_3$-2') BNA as depicted below.

(A)

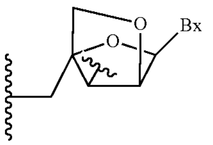

(B)

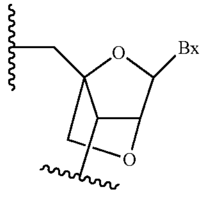

(C)

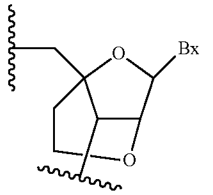

(D)

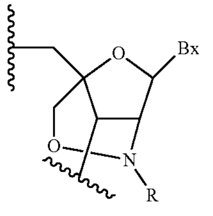

-continued (E)

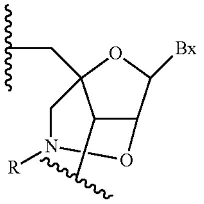

(F)

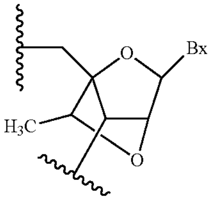

(G)

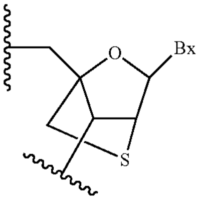

(H)

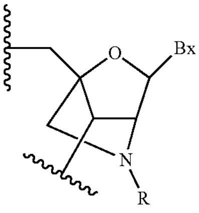

(I)

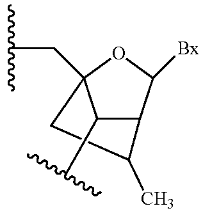

(J)

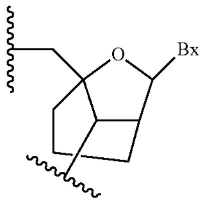

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U. S. A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 129(26) 8362-8379 (Jul. 4, 2007); Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research,* 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occuring sugar is substituted, e.g., with a sulfer, carbon or nitrogen atom. In certain such embodiments, such modified sugar moiety also comprises bridging and/or non-bridging substituents as described above. For example, certain sugar surrogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research,* 1997, 25(22), 4429-4443 and Albaek et al., *J. Org. Chem.,* 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

VII

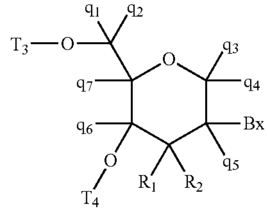

wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and q7 are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry,* 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166,315; 5,185,444; and 5,034,506). As used here, the term "morpholino" means a sugar surrogate having the following structure:

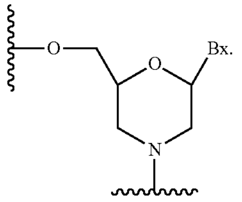

In certain embodiments, morpholinos may be modified, for example by adding or altering various substituent groups from the above morpholino structure. Such sugar surrogates are refered to herein as "modifed morpholinos."

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with ad 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Certain Nucleobases

In certain embodiments, nucleosides of the present invention comprise one or more unmodified nucleobases. In certain embodiments, nucleosides of the present invention comprise one or more modifed nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—$CH_2$—N($CH_3$)—O—$CH_2$-), thiodiester (—O—C(O)—S—), thionocarbamate (—O—C(O)(NH)—S—); siloxane (—O—Si($H)_2$—O—); and N,N'-dimethylhydrazine (—$CH_2$—N($CH_3$)—N($CH_3$)—). Modified linkages, compared to natural phosphodiester linkages, can be used to alter, typically increase, nuclease resistance of the oligomeric compound. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—N($CH_3$)—O-5'), amide-3 (3'-$CH_2$—C(═O)—N(H)-5'), amide-4 (3'-$CH_2$—N(H)—C(═O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, or 20 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisesense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxy-cholesterol moiety (Crooke et al., J. Pharmacol. Exp. Ther., 1996, 277, 923-937).

In certain embodiments, a conjugate group comprises an active drug substance, for example, aspirin, warfarin, phenylbu a7one, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group. In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments antisense compounds and antisense oligonucleotides comprise single-strand compounds. In certain embodiments antisense compounds and antisense oligonucleotides comprise double-strand compounds.

Spinal Muscular Atrophy (SMA)

SMA is a genetic disorder characterized by degeneration of spinal motor neurons. SMA is caused by the homozygous loss of both functional copies of the SMN1 gene. However, the SMN2 gene has the potential to code for the same protein as SMN1 and thus overcome the genetic defect of SMA patients. SMN2 contains a translationally silent mutation (C→T) at position +6 of exon 7, which results in inefficient inclusion of exon 7 in SMN2 transcripts. Therefore, the predominant form of SMN2, one which lacks exon 7, is unstable and inactive. Thus, therapeutic compounds capable of modulating SMN2 splicing such that the percentage of SMN2 transcripts containing exon 7 is increased, would be useful for the treatment of SMA.

In certain embodiments, the present invention provides antisense compounds complementary to a pre-mRNA encoding SMN2. In certain such embodiments, the antisense compound alters splicing of SMN2. Certain sequences and regions useful for altering splicing of SMN2 may be found in PCT/US06/024469, which is hereby incorporated by reference in its entirety for any purpose. In certain embodiments, oligomeric compounds having any motif described herein have a nucleobase sequence complementary to intron 7 of SMN2. Certain such nucleobase sequences are exemplified in the non-limiting table below.

| Sequence | Length | SEQ ID |
|---|---|---|
| TGCTGGCAGACTTAC | 15 | 82 |
| CATAATGCTGGCAGA | 15 | 83 |
| TCATAATGCTGGCAG | 15 | 84 |
| TTCATAATGCTGGCA | 15 | 85 |
| TTTCATAATGCTGGC | 15 | 86 |
| ATTCACTTTCATAATGCTGG | 20 | 87 |
| TCACTTTCATAATGCTGG | 18 | 81 |
| CTTTCATAATGCTGG | 15 | 88 |
| TCATAATGCTGG | 12 | 89 |
| ACTTTCATAATGCTG | 15 | 90 |
| TTCATAATGCTG | 12 | 91 |
| CACTTTCATAATGCT | 15 | 92 |
| TTTCATAATGCT | 12 | 93 |
| TCACTTTCATAATGC | 15 | 94 |
| CTTTCATAATGC | 12 | 95 |
| TTCACTTTCATAATG | 15 | 96 |
| ACTTTCATAATG | 12 | 97 |
| ATTCACTTTCATAAT | 15 | 98 |
| CACTTTCATAAT | 12 | 99 |
| GATTCACTTTCATAA | 15 | 100 |
| TCACTTTCATAA | 12 | 101 |
| TTCACTTTCATA | 12 | 102 |
| ATTCACTTTCAT | 12 | 103 |
| AGTAAGATTCACTTT | 15 | 104 |

Antisense compounds of the present invention can be used to modulate the expression of SMN2 in a subject, such as a human. In certain embodiments, the subject has spinal muscular atrophy. In certain such subjects, the SMN1 gene is absent or otherwise fails to produce sufficient amounts of functional SMN protein. In certain embodiments, the antisense compounds of the present invention effectively modulate splicing of SMN2, resulting in an increase in exon 7 inclusion in SMN2 mRNA and ultimately in SMN2 protein that includes the amino acids corresponding to exon 7. Such alternate SMN2 protein resembles wild-type SMN protein. Antisense compounds of the present invention that effectively modulate expression of SMN2 mRNA or protein products of expression are considered active antisense compounds.

Modulation of expression of SMN2 can be measured in a bodily fluid, which may or may not contain cells; tissue; or organ of the animal. Methods of obtaining samples for analysis, such as body fluids (e.g., sputum, serum, CSF), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers associated with the target gene expression in the aforementioned fluids, tissues or organs, collected from an animal contacted with one or more compounds of the invention, by routine clinical methods known in the art.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of SMN2 expression in the cells of bodily fluids, organs or tissues. An effective amount can be determined by monitoring the modulatory effect of the antisense compound or compounds or compositions on target nucleic acids or their products by methods routine to the skilled artisan.

The invention also provides an antisense compound as described herein, for use in any of the methods as described herein. For example, the invention provides an antisense compound comprising an antisense oligonucleotide complementary to a nucleic acid encoding human SMN2, for use in treating a disease or condition associated with survival motor neuron protein (SMN), such as spinal muscular atrophy (SMA). As a further example, the invention provides an antisense compound comprising an antisense oligonucleotide complementary to a nucleic acid encoding human SMN2, for use in treating a disease or condition associated with survival motor neuron protein (SMN) by administering the antisense compound directly into the central nervous system (CNS) or CSF.

The invention also provides the use of an antisense compound as described herein in the manufacture of a medicament for use in any of the methods as described herein. For example, the invention provides the use of an antisense compound comprising an antisense oligonucleotide complementary to a nucleic acid encoding human SMN2 in the manufacture of a medicament for treating a disease or condition associated with survival motor neuron protein (SMN), such as spinal muscular atrophy (SMA). As a further example, the invention provides the use of an antisense compound comprising an antisense oligonucleotide complementary to a nucleic acid encoding human SMN2 in the manufacture of a medicament for treating a disease or condition associated with survival motor neuron protein (SMN) by administration of the medicament directly into the central nervous system (CNS) or CSF.

Certain Target Nucleic Acids and Mechanisms

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a long non-coding RNA. In certain embodiments, the target nucleic acid is a SMN-NAT transcript. In certain embodiments, the target RNA has the sequence set forth in SEQ ID NO. 1.

In certain embodiments, natural antisense transcripts (NATs) are RNA transcripts encoded within a cell that have transcript complementarity to other RNA transcripts. In certain embodiments, natural antisense transcripts may play one or more roles in regulating expression of complementary RNA transcripts. For example, in certain embodiments, a natural antisense transcripts may serve to partially silence the expression of its complementary RNA transcript. Therefore, reducing the expression of certain natural antisense transcripts may increase expression of certain complementary RNA transcripts.

SMA is caused by the loss of both copies of survival motor neuron gene 1 (SMN1), which may also be known as SMN Telomeric, a protein that is part of a multi-protein complex thought to be involved in snRNP biogenesis and recycling. A nearly identical gene, SMN2, which may also be known as SMN Centromeric, exists in a duplicated region on chromosome 5q13 and modulates disease severity. Although SMN1 and SMN2 have the potential to code for the same protein, SMN2 contains a translationally silent mutation at position +6 of exon 7, which results in inefficient inclusion of exon 7 in SMN2 transcripts. In certain embodiments, a natural antisense transcript to SMN exists (e.g. SMN-NAT), and SMN-NAT is complementary to both SMN1 and SMN2. Therefore, in certain embodiments, SMN-NAT reduces expression of SMN1 and SMN2.

In instances where loss of SMN1 has occurred, SMN-NAT will reduce expression of SMN2, which may exacerbate symptoms associated with Spinal Muscular Atrophy. As discussed above, the severity of Spinal Muscular Atrophy correlates to the amount of function SMN protein produced by SMN2. Therefore, in certain embodiments, it is desirable to increase expression of SMN2. Although SMN2 contains a translationally silent mutation at position +6 of exon 7, which results in inefficient inclusion of exon 7 in SMN2 transcripts, the SMN2 gene will produce copies of functional SMN (e.g. SMN mRNA containing exon 7, which are then translated into full-length SMN protein). In certain embodiments, increased expression of SMN2 results in increased amounts of functional SMN protein containing amino acids encoded by exon 7. In certain embodiments, reduction of SMN-NAT increases expression of SMN2 and increases the amount of functional SMN protein.

Certain embodiments disclosed herein are drawn to a method of inducing expression of SMN in a cell comprising contacting the cell with an antisense compound targeted to SMN-NAT. In several aspects, SMN-NAT comprises a nucleic acid sequence at least 85% identical to SEQ ID NO:1.

Certain Combinations and Combination Therapies

In certain embodiments, a first antisense compound targeted to SMN-NAT is co-administered with a second antisense compound targeted to SMN. In certain embodiments, the first antisense compound targeted to SMN-NAT will reduce expression of SMN-NAT and thereby increase expression of full length SMN2 pre-mRNA. The second antisense compound is targeted to SMN2 pre-mRNA and is designed to modulate splicing of SMN2 pre-mRNA. Thus the first antisense compound increases expression of total SMN2 pre-mRNA and the second antisense compound modulates the splicing of the SMN2 pre-mRNA to increase the amount of SMN2 mRNA that includes exon 7.

In certain embodiments, the first antisense compound is a gapmer designed to elicit RNase H cleavage of an SMN-NAT transcript and the second antisense compound is designed to alter splicing or SMN2 pre-mRNA.

In certain embodiments, the first antisense compound is a modified oligonucleotide having a nucleobase sequence consisting of a sequence selected from among SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

In certain embodiments, the second antisense compound is a modified oligonucleotide having a nucleobase sequence consisting of a sequence selected from among SEQ ID NOs: 81, 82, 83, 84, 85, 86, 87, 88, 89, 90, 91, 92, 93, 94, 95, 96, 97, 98, 99, 100, 101, 102, 103, or 104.

In certain embodiments, the first antisense compound and the second antisense compound are administered at the same time. In certain embodiments, the first antisense compound and the second antisense compound are administered in a single dose. In certain embodiments, the first antisense compound and the second antisense compound are administered sequentially.

Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the eyes, ears).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited herein is hereby incorporated by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other unmodified bases, such as "AT$^{me}$CGAUCG," wherein $^{me}$C indicates a cytosine base comprising a methyl group at the 5-position.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1

Effect of Antisense Oligonucleotides Targeting SMN-NAT

Antisense oligonucleotides were designed targeting the SMN-NAT sequence, described herein as SEQ ID NO: 1 (GenBank accession #BC045789.1) and were tested for their effects on reducing the expression of SMN-NAT in HEK293T cells. As shown in Table 1, antisense oligonucleotides are effective at reducing expression of SMN-NAT.

The newly designed antisense oligonucleotides in Table 1 were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P═S) linkages. All cytosine residues throughout each gapmer are 5-methylcytosines.

TABLE 1

Antisense oligonucleotides targeted to SMN-NAT

| IsisNo | Sequence | % Reduction of SMN-NAT | Start Site Seq ID: 1 | Stop Site Seq ID: 1 | SEQ ID NO. |
|---|---|---|---|---|---|
| 658741 | GTACTACACTTTTAATTACT | 0.00 | 1 | 20 | 3 |
| 658742 | TGTATATTGATGTCAGTACT | 9.81 | 16 | 35 | 4 |
| 658743 | TACATTGTCTATTAGTGTAT | 0.00 | 31 | 50 | 5 |
| 658744 | TGACTCTCAATTCTGTTACA | 0.00 | 47 | 66 | 6 |
| 658745 | TCACAGGGCTATTTCTGACT | 0.00 | 62 | 81 | 7 |
| 658746 | AATCAGTCACATATATCACA | 70.85 | 77 | 96 | 8 |
| 658747 | TGTAACTTTAGTTAAAATCA | 60.93 | 92 | 111 | 9 |
| 658748 | CTATTAAACCACATTTGTAA | 32.31 | 107 | 126 | 10 |
| 658749 | ACTACTATGCTTTCTCTATT | 0.00 | 122 | 141 | 11 |
| 658750 | CCACCATTTCTTGAAACTAC | 0.00 | 137 | 156 | 12 |
| 658751 | TTTCCAATAGTTTTACCACC | 0.00 | 152 | 171 | 13 |
| 658752 | GTTTTTGCATAAGGATTTCC | 26.89 | 167 | 186 | 14 |
| 658753 | GTGGAAATTTGGTTTGTTTT | 0.00 | 182 | 201 | 15 |
| 658754 | TGTGGCTCAGTGTAGGTGGA | 0.00 | 197 | 216 | 16 |
| 658755 | GTATTAATTCTTATATGTGG | 0.00 | 212 | 231 | 17 |
| 658756 | TTAGTTTTACACTTAGGTCT | 11.16 | 244 | 263 | 18 |
| 658757 | ACACAGTTTAGAGTTTTAGT | 0.00 | 259 | 278 | 19 |
| 658758 | GATCACAGATTTTTCTCTCT | 38.43 | 290 | 309 | 20 |
| 658759 | TTATAGGCAATCCATGATCA | 20.70 | 305 | 324 | 21 |

TABLE 1-continued

Antisense oligonucleotides targeted to SMN-NAT

| IsisNo | Sequence | % Reduction of SMN-NAT | Start Site Seq ID: 1 | Stop Site Seq ID: 1 | SEQ ID NO. |
|---|---|---|---|---|---|
| 658760 | CATTTCAGTTTGTTCTTTTG | 53.97 | 325 | 344 | 22 |
| 658761 | CCCAGGCAACAAGGCCATTT | 16.58 | 340 | 359 | 23 |
| 658762 | GAACCTCGGGTGCCACCCCA | 0.00 | 356 | 375 | 24 |
| 658763 | CGTCCTTGATTTCCTCAGCG | 25.83 | 385 | 404 | 25 |
| 658764 | ACACCCTTGGTGTGTCAGCG | 35.68 | 403 | 422 | 26 |
| 658765 | TTCTGCTCTAGCCTCACACC | 0.00 | 418 | 437 | 27 |
| 658766 | GGAGAGAGCTAGTCTCTTTC | 0.00 | 453 | 472 | 28 |
| 658767 | AGGACCTCTCTCTGCAGGAG | 74.78 | 469 | 488 | 29 |
| 658768 | ATGGGAACTCTTTTCAGGAC | 0.00 | 484 | 503 | 30 |
| 658769 | GCATTTCACTGTGGAATGGG | 0.00 | 499 | 518 | 31 |
| 658770 | TTTATAAAAATGCTTGCATT | 81.60 | 514 | 533 | 32 |
| 658771 | CTTCCCATTAGCTCATTTAT | 68.30 | 529 | 548 | 33 |
| 658772 | TAGATAAGCTACCCCCTTCC | 0.00 | 544 | 563 | 34 |
| 658773 | TTTGCTCCCTATGTGTAGAT | 34.09 | 559 | 578 | 35 |
| 658774 | GGTCCTAACTGGTTTTTTGC | 55.30 | 574 | 593 | 36 |
| 658775 | CAGATGGCAACACCTGGTCC | 0.00 | 589 | 608 | 37 |
| 658776 | GATTCACGCTCTGTGCAGAT | 0.00 | 604 | 623 | 38 |
| 658777 | GCCTGCATAATAAAAGGTTG | 0.00 | 641 | 660 | 39 |
| 658778 | TCAGGCCAAGGACCTGCCTG | 73.05 | 656 | 675 | 40 |
| 658779 | TAAGCAATGTGGAGTAGCTC | 45.19 | 674 | 693 | 41 |
| 658780 | ACAATAGGAAAGAGATAAGC | 46.19 | 689 | 708 | 42 |
| 658781 | TTATTTAGCACATGCACAAT | 0.00 | 704 | 723 | 43 |
| 658782 | TGGCTCCACCTCCCCTTATT | 4.82 | 719 | 738 | 44 |
| 658783 | GCATGTCCACCATGGTGGCT | 92.56 | 734 | 753 | 45 |
| 658784 | AGCTGCACGGAGAGAAAGGG | 47.38 | 768 | 787 | 46 |
| 658785 | GCATGTTGTGAGTTGTTGGG | 0.00 | 797 | 816 | 47 |
| 658786 | TCAGATAAGGAAGCTGGAAG | 0.00 | 820 | 839 | 48 |
| 658787 | GACCTTAGTACATACTCAGA | 0.00 | 835 | 854 | 49 |
| 658788 | GAAGTAAACACAGTGGACCT | 0.00 | 850 | 869 | 50 |
| 658789 | GTATGTGAAGTAAACACAGT | 0.00 | 856<br>874 | 875<br>893 | 51 |
| 658790 | GTAAACACAGTATGTGAAGT | 56.26 | 865 | 884 | 52 |
| 658791 | AGGTGGGTATGTGAAGTAAA | 0.00 | 880 | 899 | 53 |
| 658792 | ATCAGCAAGCTTCACATACG | 20.31 | 902 | 921 | 54 |
| 658793 | GGAGCTTCCTGGGTAATCAG | 0.00 | 917 | 936 | 55 |
| 658794 | AGCAGCTCTGGCACAGAGGG | 0.00 | 937 | 956 | 56 |
| 658795 | AAACATGTATAAGGAAGCAG | 52.59 | 952 | 971 | 57 |

TABLE 1-continued

| Antisense oligonucleotides targeted to SMN-NAT | | | | | |
|---|---|---|---|---|---|
| IsisNo | Sequence | % Reduction of SMN-NAT | Start Site Seq ID: 1 | Stop Site Seq ID: 1 | SEQ ID NO. |
| 658796 | GGAAGATCGGGCTGTAAACA | 54.20 | 967 | 986 | 58 |
| 658797 | ACTTCTCTTCTAACAAGGAG | 73.05 | 993 | 1012 | 59 |
| 658798 | CAGAGTCCTCGGTAGAACTT | 91.02 | 1043 | 1062 | 60 |
| 658799 | AAGCCGATAGTTAGACAGAG | 0.00 | 1058 | 1077 | 61 |
| 658800 | AAAAAAAGACTAGGTAAGCC | 0.00 | 1073 | 1092 | 62 |
| 658801 | GTTTTGAGAGAGGAGGTAAA | 15.76 | 1090 | 1109 | 63 |
| 658802 | GTTTTTTCTTTGATGGTTTT | 66.43 | 1105 | 1124 | 64 |
| 658803 | GAAATCTAATTTTTCAGTTT | 93.98 | 1121 | 1140 | 65 |
| 658804 | AATCTTAATTTTGCTGAAAT | 37.35 | 1136 | 1155 | 66 |
| 658805 | TTTTTAAGAACAGAAAATCT | 57.27 | 1151 | 1170 | 67 |
| 658806 | ACACTTTGGTTTTTCATTTT | 60.18 | 1183 | 1202 | 68 |
| 658807 | ATTTTCTCCCGGTTTACACT | 60.00 | 1198 | 1217 | 69 |
| 658808 | AGGTAACTTGCATGTATTTT | 0.00 | 1213 | 1232 | 70 |
| 658809 | AATATCTTTATCAGATAGGT | 0.00 | 1229 | 1248 | 71 |
| 658810 | ATGTTTGCTGGGTACAATAT | 51.71 | 1244 | 1263 | 72 |
| 658811 | GTTTGAGAGTTCTTCATGTT | 0.00 | 1259 | 1278 | 73 |
| 658812 | CATCTTTTAATTGAATTTTT | 0.00 | 1290 | 1309 | 74 |
| 658813 | CCCGGCCAACTTACCCATCT | 0.00 | 1305 | 1324 | 75 |
| 658814 | GATTGGGATTGCAAGTATGA | 0.00 | 1334 | 1353 | 76 |
| 658815 | GAGCACACGCCACAATGCCT | 0.90 | 1456 | 1475 | 77 |
| 658816 | AGTCTTCTTGTCTCAGCCTT | 0.00 | 1494 | 1513 | 78 |
| 658817 | CCACCTCCTGCGCTCAGTCT | 0.00 | 1509 | 1528 | 79 |
| 658818 | TCACACAGCCTACTGCAGCC | 0.00 | 1530 | 1549 | 80 |

Example 2

Effect of Antisense Oligonucleotides Targeting SMN-NAT on SMN RNA

Two antisense oligonucleotides from Example 1 above, Isis Nos. 658803 and 658798 were chosen for further evaluation for effects on increasing SMN transcription in HEK293T cells. A scrambled ASO not complementary to SMN-NAT was used as a control. HEK293T cells were transfected with Lipofectamine-2000 (Life Technologies) according to manufacturer's instructions and RNA was collected 24 hours after transfection. Standard RT-qPCR was used to assess SMN-NAT, SMN pre-mRNA and FL-SMN (full-length SMN) mRNA levels. As shown in Table 2, antisense oligonucleotides designed to reduce expression of SMN-NAT can effectively increase expression of SMN pre-mRNA and full length SMN mRNA in a dose dependent manner.

TABLE 2

| Effect of antisense oligonucleotides targeting SMN-NAT | | | | |
|---|---|---|---|---|
| | | Relative Levels | | |
| Isis No. | Dose | SMN-NAT | SMN pre-mRNA | FL-SMN mRNA |
| 141923 | 0 nM | 1.13 | 0.85 | 0.95 |
| | 62.5 nM | 1.10 | 1.00 | 1.12 |
| | 12 5 nM | 1.15 | 0.86 | 1.23 |
| | 250 nM | 0.99 | 1.05 | 0.97 |
| | 500 nM | 1.13 | 1.03 | 1.13 |
| 658803 | 0 nM | 0.99 | 1.12 | 1.00 |
| | 62.5 nM | 0.58 | 1.05 | 1.16 |
| | 125 nM | 0.48 | 1.36 | 1.39 |
| | 250 nM | 0.31 | 1.68 | 1.83 |
| | 500 nM | 0.16 | 1.63 | 1.65 |
| 658798 | 0 nM | 1.03 | 0.95 | 1.03 |
| | 62.5 nM | 0.84 | 1.10 | 1.03 |
| | 125 nM | 0.69 | 1.30 | 1.29 |
| | 250 nM | 0.52 | 1.61 | 1.49 |
| | 500 nM | 0.31 | 1.58 | 1.74 |

Example 3

Effect of Antisense Oligonucleotides Targeting SMN-NAT on SMN RNA in SMA Fibroblasts Antisense oligonucleotide Isis No 658803 was used in a SMA fibroblast line (GM03813, Coriell) and in a carrier fibroblast line (GM03814, Coriell). Fibroblasts were transfected with Cytofectin with various concentrations (0 nM to 100 nM) of antisense oligonucleotide. Forty-eight hours after transfection, protein lysates were collected and SMN protein levels were determined by Western blot analysis. Histone H3 was used as a loading control. Signal intensity was determined using ImageJ gel analysis tool (NIH) and SMN levels were normalized to H3 levels. As shown in Table 3, antisense oligonucleotides designed to reduce expression of SMN-NAT increased expression of SMN protein in a dose dependent manner.

TABLE 3

| Antisense oligonucleotides targeting SMN-NAT in SMA Fibroblasts | | | |
|---|---|---|---|
| | | Relative SMN protein Levels (AU) | |
| Isis No. | Dose (nM) | GM03813 SMA | GM03814 Carrier |
| Isis No. 658803 | 0 | 1.00 | 1.86 |
| | 6 | 1.19 | 2.09 |
| | 12 | 1.19 | 2.16 |
| | 25 | 1.85 | 1.98 |
| | 50 | 1.98 | 2.12 |
| | 100 | 1.18 | 2.15 |

Example 4

Effect of Antisense Oligonucleotides Targeting SMN-NAT on SMN RNA in Primary SMA Neurons Antisense oligonucleotide Isis No 658803 was used to evaluate levels of SMN pre-mRNA and FL-SMN mRNA in primary cortical neurons isolated from E13.5 embryos of SMA mice (the SMN Δ7 mouse model, Stock number 005025, The Jackson laboratory). Five μM antisense oligonucleotide was added to the growth medium 2 days after plating out and incubated for 4 days. SMN-NAT, SMN pre-mRNA and FL-SMN mRNA levels were measured using RT-qPCR. As shown in Table 4 below, antisense oligonucleotides designed to reduce expression of SMN-NAT increased expression of SMN pre-mRNA and full length SMN mRNA in primary SMA neurons.

TABLE 4

Effect of antisense oligonucleotides targeting SMN-NAT on SMN RNA in Primary SMA neurons

| | Relative Levels | | |
|---|---|---|---|
| Isis No. | SMN-NAT | SMN pre-MRNA | FL-SMN mRNA |
| Untreated | 0.98 | 1.06 | 1.13 |
| 141923 (scrambled) | 1.01 | 1.13 | 1.11 |
| 658803 | 0.35 | 1.94 | 1.79 |

Example 5

Dose Response of Antisense Oligonucleotides Targeting SMN-NAT in HeLa Cells

SMN-NAT targeting antisense oligonucleotides selected from Table 1 were tested for dose response analysis in HeLa cells. Oligonucleotide Scrbl, which does not target SMN-NAT, and Isis Number 387954, which targets SMN pre-mRNA,were used as negative controls. Cells were electroporated with 0, 6, 12, 25, 50, or 100 nM of antisense oligonucleotide, and SMN-NAT mRNA was analyzed as described in Example 2. Results are presented in Table 5 below. The results show that the antisense oligonucleotides targeting SMN-NAT inhibited SMN-NAT mRNA expression in a dose dependent manner.

TABLE 5

Effect of antisense oligonuclotides targeting SMN-NAT on SMN RNA in HeLa Cells

| Isis No. | Dose (nM) | SMN-NAT Relative levels |
|---|---|---|
| 658761 | 0 | 0.99 |
| | 6 | 0.89 |
| | 12 | 0.67 |
| | 25 | 0.45 |
| | 50 | 0.37 |
| | 100 | 0.22 |
| 658764 | 0 | 1.09 |
| | 6 | 0.67 |
| | 12 | 0.54 |
| | 25 | 0.44 |
| | 50 | 0.43 |
| | 100 | 0.32 |
| 658765 | 0 | 1.09 |
| | 6 | 0.88 |
| | 12 | 0.79 |
| | 25 | 0.63 |
| | 50 | 0.51 |
| | 100 | 0.44 |
| 658792 | 0 | 2.02 |
| | 6 | 1.06 |
| | 12 | 0.83 |
| | 25 | 0.52 |
| | 50 | 0.36 |
| | 100 | 0.25 |
| 658798 | 0 | 1.05 |
| | 6 | 0.83 |
| | 12 | 0.74 |
| | 25 | 0.52 |
| | 50 | 0.35 |
| | 100 | 0.22 |

TABLE 5-continued

Effect of antisense oligonuclotides targeting SMN-NAT on SMN RNA in HeLa Cells

| Isis No. | Dose (nM) | SMN-NAT Relative levels |
|---|---|---|
| 658802 | 0 | 1.02 |
| | 6 | 0.95 |
| | 12 | 0.66 |
| | 25 | 0.49 |
| | 50 | 0.41 |
| | 100 | 0.17 |
| 658803 | 0 | 0.98 |
| | 6 | 0.86 |
| | 12 | 0.70 |
| | 25 | 0.47 |
| | 50 | 0.41 |
| | 100 | 0.25 |
| 658815 | 0 | 1.05 |
| | 6 | 0.83 |
| | 12 | 0.55 |
| | 25 | 0.45 |
| | 50 | 0.36 |
| | 100 | 0.32 |
| Scrb1 | 0 | 0.94 |
| | 6 | 1.09 |
| | 12 | 0.89 |
| | 25 | 1.00 |
| | 50 | 1.12 |
| | 100 | 1.07 |
| 387954 | 0 | 1.12 |
| | 6 | 1.23 |
| | 12 | 1.30 |
| | 25 | 1.19 |
| | 50 | 1.21 |
| | 100 | 1.07 |

Example 6

Effect of Antisense Oligonucleotides on SMN-NAT in SMA Mice

Antisense oligonucleotides targeting the SMN-NAT sequence, described herein as SEQ ID NO: 1 (GenBank accession #$BC_{045789.1}$) were tested for their effects on SMN-NAT expression in adult SMA mice.

The antisense oligonucleotides in Table 6 were designed as 5-10-5 MOE gapmers having a mixed backbone (MBB). The gapmers are 20 nucleosides in length, wherein the central gap segment comprises ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are each independently selected from phosphorothioate (P═S) linkages and phosphodiester linkages. A subscript "o" denotes the location of the phosphodiester internucleoside linkages, all other internucleoside linkages are P═S linkages. All cytosine residues throughout each gapmer are 5-methylcytosines.

TABLE 6

Antisense oligonucleotides targeted to SMN-NAT

| Isis No | Sequence | Start Site Seq ID: 1 | Stop Site Seq ID: 1 | SEQ ID NO. |
|---|---|---|---|---|
| 813208 | $CA_oG_oA_oG_oTCCTCGGTAGA_oA_oCTT$ | 1043 | 1062 | 60 |
| 813209 | $GA_oA_oA_oT_oCTAATTTTTCA_oG_oTTT$ | 1121 | 1140 | 65 |

Adult SMA mice (Jax #005058) received an intracerebroventricular (ICV) injection of 500 μg antisense oligonucleotide in PBS or an injection of PBS only. After 15 days, the mice were euthanized and total RNA and protein were isolated from the brain and spinal cord. SMN-NAT RNA levels and FL-SMN2 RNA levels were measured by RT-qPCR as described in example 2. The SMN/GAPDH protein ratio was measured by western blot analysis using antibodies against SMN and GAPDH. Signal intensity was measured with ImageJ gel analysis tool, and SMN values were normalized to GAPDH values. Isis No. 449323, which targets SMN pre-mRNA and corrects splicing was included as a positive control.

TABLE 7

Effect of antisense oligonucleotides on SMN-NAT expression in adult SMA mice

| | Relative Levels in the Brain | | | Relative Levels in the Spinal Cord | | |
|---|---|---|---|---|---|---|
| Isis No. | SMN-NAT | FL-SMN2 mRNA | SMN/GADPH | SMN-NAT | FL-SMN2 mRNA | SMN/GADPH |
| PBS | 0.97 | 1.03 | 0.91 | 1.02 | 1.08 | 0.21 |
| 449323 | 1.05 | 3.08 | 1.38 | 1.04 | 3.18 | 0.58 |
| 813208 | 0.41 | 1.05 | 0.65 | 0.65 | 0.97 | 0.18 |
| 813209 | 0.30 | 0.93 | 0.64 | 0.36 | 0.95 | 0.21 |

Example 7

Effect of Systemic Administration of Antisense Oligonucleotides on Neonatal SMA Mice Groups of 3 SMA mice (Jax #005025) received a single subcutaneous dose of 300 ug/g of an antisense oligonucleotide (ASO) listed in the table below on post-natal day 1 and a second dose of 300 ug/g ASO on post-natal day 3. Each group of mice received either a scrambled control ASO (Isis No. 141923), an ASO designed to knock down SMN-NAT (Isis No. 813208), or an SMN2 splicing ASO (Isis No. 449323). A group of 3 wild-type mice that did not receive any treatment was also used as a control (WT). After 10 days, the mice were sacrificed and relative levels of SMN-NAT, FL-SMN2 mRNA, and SMN protein relative to GAPDH were measured by RT-qPCR in both the brain and spinal cord.

TABLE 8

Effect of systemic administration of antisense oligonucleotides on SMN-NAT expression in SMA mice

| | | Relative Levels in the Brain | | | Relative Levels in the Spinal Cord | | |
|---|---|---|---|---|---|---|---|
| Isis No. | Mouse genotype | SMN-NAT | FL-SMN2 mRNA | SMN/GADPH | SMN-NAT | FL-SMN2 mRNA | SMN/GAPDH |
| N/A | WT | 1.09 | 1.06 | 2.38 | 0.81 | 1.15 | 1.68 |
| 141923 | SMA | 1.11 | 1.07 | 0.93 | 1.00 | 1.32 | 0.65 |
| 449323 | SMA | 1.09 | 1.59 | 1.90 | 0.83 | 1.79 | 1.51 |
| 813208 | SMA | 0.72 | 1.32 | 1.34 | 0.58 | 1.99 | 0.95 |

Example 8

Effect of Antisense Oligonucleotides Targeting Human SMN2 in an SMA Type III Mice Model Taiwan strain of SMA type III mice were obtained from The Jackson Laboratory (Bar Harbor, Me.). These mice lack mouse SMN and are homozygous for human SMN2 (mSMN −/−; hSMN2 +/+). These mice have been described in Hsieh-Li H M, et al., *Nature Genet.* 24, 66-70 2000. Antisense oligonucleotides targeting human SMN2 were designed and tested in these mice.

The antisense oligonucleotides in the Table below were designed as uniform 2'-MOE oligonucleotides with mixed backbone chemistry. Each antisense oligonucleotide is 18 nucleosides in length and each nucleoside has a 2'-MOE sugar modification. The internucleoside linkages throughout each gapmer are either phosphodiester or phosphorothioate linkages. The internucleoside linkages of each oligonucleotide is denoted in the Backbone Chemistry column, where 'o' indicates a phosphodiester linkage and 's' indicates a phosphorothioate linkage. All cytosine residues throughout each oligonucleotide are 5-methylcytosines. Each antisense oligonucleotide listed in the Table below is targeted to the human SMN2 genomic sequence, designated herein as SEQ ID NO: 2 (GENBANK Accession No. NT_006713.14 truncated from nucleotides 19939708 to 19967777) at the target region 27062-27079.

TABLE 9

Modified oligonucleotides targeting human SMN2 with mixed backbone chemistry

| ISIS No | Sequence | Backbone Chemistry | SEQ ID NO |
|---|---|---|---|
| 449320 | TCACTTTCATAATGCTGG | ssooooooooooooooss | 81 |
| 449323 | TCACTTTCATAATGCTGG | sosososososososos | 81 |

TABLE 9-continued

| Modified oligonucleotides targeting human SMN2 with mixed backbone chemistry | | | |
|---|---|---|---|
| ISIS No | Sequence | Backbone Chemistry | SEQ ID NO |
| 605918 | TCACTTTCATAATGCTGG | sssosososososososss | 81 |
| 605919 | TCACTTTCATAATGCTGG | sooosssssssssoooss | 81 |

Treatment

Mice were administered 500 μg of ISIS oligonucleotide by intracerebroventricular (ICV) bolus injection. Control mice were administered PBS alone (dose of 0).

Tolerability Assay

At 3 hours post injection, each mouse was evaluated according to 7 different criteria. The 7 criteria are (1) the mouse was bright, alert, and responsive; (2) the mouse was standing or hunched without stimuli; (3) the mouse shows any movement without stimuli (4) the mouse demonstrates forward movement after its lifted; (5) the mouse demonstrates any movement after its lifted; (6) the mouse responds to a tail pinch; (7) regular breathing. For each of the 7 different criteria, each mouse was given a sub-score of 0 if it met the criteria or 1 if it did not. After all of the 7 criteria were evaluated, the sub-scores were summed for each mouse and then averaged for each group. For example, if a mouse was bright, alert, and responsive 3 hours after the ICV dose, and met all other criteria, it would get a summed score of 0. If another mouse was not bright, alert, and responsive 3 hours after the ICV dose but met all other criteria, it would receive a score of 1. Saline treated mice generally receive a score of 0. As presented in the Table below, the ISIS oligonucleotides were deemed tolerable in the transgenic mice.

TABLE 10

| Scoring for tolerability to ISIS oligonucleotides in SMA Type III mice | |
|---|---|
| ISIS No | 3 hr Score |
| 449320 | 0 |
| 449323 | 0 |
| 605918 | 3 |
| 605919 | 0 |

Exon 7 Splicing

Animals were sacrificed 2 weeks after the injection and brain and lumbar sections of the spinal cords were collected from each animal. Real time PCR was performed on each sample to determine the amount of human SMN2 message including exon 7 (exon $7^+$) and the amount of human SMN2 message lacking exon 7(exon $7^-$). Expression levels for exon $7^+$ and exon $7^-$ were normalized to total SMN2 levels. The data presented in the Table below are expressed as exon $7^+$ and exon $7^-$ levels divided by total SMN levels, and were further normalized to the levels obtained in the PBS control group (designated as 1).

Administration of ISIS oligonucleotides targeting SEQ ID NO: 2 at start site 27062, but with different backbone chemistries, all resulted in a striking increase in inclusion of exon 7.

TABLE 11

| Effect of ISIS oligonucleotides targeting SMN2 on splicing in SMA Type III Mice | | | | |
|---|---|---|---|---|
| | Brain | | Lumbar Cord | |
| | exon $7^+$ | exon $7^-$ | exon $7^+$ | exon $7^-$ |
| PBS | 1.0 | 1.0 | 1.0 | 1.0 |
| 449320 | 2.4 | 0.60 | 2.7 | 0.66 |
| 449323 | 4.3 | 0.24 | 4.5 | 0.33 |
| 605918 | 4.4 | 0.23 | 4.5 | 0.28 |
| 605919 | 4.2 | 0.26 | 4.0 | 0.38 |

Example 9

Effect of Systemic Administration of an Antisense Oligonucleotide Targeted to SMN-NAT and an Antisense Oligonucleotide Targeted to SMN in SMA Mice The Examples above illustrate that targeting the SMN-NAT transcript with an antisense oligonucleotide can reduce expression of SMN-NAT and increase expression of SMN pre-mRNA and full length SMN mRNA (see, e.g. Example 4). The Examples above also illustrate that antisense oligonucleotides targeted to the SMN2 transcript can alter splicing of the SMN2 transcript to increase inclusion of Exon 7 (see, e.g. Example 7). Therefore, in certain embodiments one an antisense oligonucleotide may be used to increase expression of SMN2 pre-mRNA via knocking down the SMN-NAT transcript, and another antisense oligonucleotide can alter the splicing of the increased amount of SMN2 transcript by increasing exon 7 inclusion.

A group of 3 SMA mice (Jax #005025) received a single subcutaneous dose of 400 ug/g of an antisense oligonucleotide ISIS 813208 (ASO) on post-natal day 1 and a second dose of 400 ug/g ASO on post-natal day 3. Concurrent with administration of ISIS 813208 on days P1 and P3, each mouse also received a single subcutaneous dose of 50 ug/g of ISIS 449323. Thus each mouse in this group received a dose of ISIS 813208 designed to decrease SMN-NAT expression and a dose of ISIS 449323 designed to increase inclusion of exon 7 of the SMN pre-mRNA. Another group of mice received a single subcutaneous dose of 50 ug/g of ISIS 449323 on P1 and P3 along with a dose of saline on P1 and P3. A third group of mice received a dose of saline only on P1 and P3. After 10 days, the mice were sacrificed and relative levels of SMN-NAT, SMN pre-mRNA, FL-SMN2 mRNA, and SMN2-Δ7 mRNA relative to GAPDH were measured by RT-qPCR in the brain, spinal cord, liver and kidney. The results are presented in the tables below:

TABLE 12

| Relative Levels in the Brain | | | | |
|---|---|---|---|---|
| | Relative Levels in the Brain | | | |
| Isis No. | SMN-NAT | SMN pre-mRNA | FL-SMN2 mRNA | SMN2 −Δ7 mRNA |
| Saline + Saline | 0.99 | 0.99 | 1.08 | 1.15 |
| 449323 + Saline | 0.91 | 1.22 | 1.46 | 0.80 |
| 449323 + 813208 | 0.32 | 3.01 | 2.49 | 1.02 |

TABLE 13

| Relative Levels in the Spinal Cord | | | | |
|---|---|---|---|---|
| | Relative Levels in the Spinal cord | | | |
| Isis No. | SMN-NAT | SMN pre-mRNA | FL-SMN2 mRNA | SMN2 -Δ7 mRNA |
| Saline + Saline | 0.88 | 0.80 | 1.64 | 1.02 |
| 449323 + Saline | 0.86 | 1.04 | 3.26 | 0.94 |
| 449323 + 813208 | 0.50 | 0.71 | 4.87 | 0.86 |

TABLE 14

| Relative Levels in the Liver | | | | |
|---|---|---|---|---|
| | Relative Levels in the Liver | | | |
| Isis No. | SMN-NAT | SMN pre-mRNA | FL-SMN2 mRNA | SMN2 -Δ7 mRNA |
| Saline + Saline | 0.10 | 1.23 | 0.58 | 0.88 |
| 449323 + Saline | 0.07 | 0.50 | 4.90 | 0.58 |
| 449323 + 813208 | 0.04 | 0.38 | 5.51 | 0.63 |

TABLE 15

| Relative Levels in the Kidney | | | | |
|---|---|---|---|---|
| | Relative Levels in the Kidney | | | |
| Isis No. | SMN-NAT | SMN pre-mRNA | FL-SMN2 mRNA | SMN2 -Δ7 mRNA |
| Saline + Saline | 0.03 | 0.54 | 0.42 | 0.80 |
| 449323 + Saline | 0.03 | 0.44 | 1.11 | 0.83 |
| 449323 + 813208 | 0.01 | 0.37 | 1.17 | 0.71 |

Example 10

Effect on Survival, Lifespan, and Body Weight of Systemic Administration of an Antisense Oligonucleotide Targeted to SMN-NAT and an Antisense Oligonucleotide Targeted to SMN in SMA Mice A group of 14 SMA mice (Jax #005025) received a single subcutaneous dose of 400 ug/g of an antisense oligonucleotide ISIS 813208 (ASO) on post-natal day 1 and a second dose of 400 ug/g ASO on post-natal day 3. Concurrent with administration of ISIS 813208 on days P1 and P3, each mouse also received a single subcutaneous dose of 50 ug/g of ISIS 449323. Thus each mouse in this group received a dose of ISIS 813208 designed to decrease SMN-NAT expression and a dose of ISIS 449323 designed to increase inclusion of exon 7 of the SMN pre-mRNA. Another group of 15 mice received a single subcutaneous dose of 50 ug/g of ISIS 449323 on P1 and P3 along with a dose of saline on P1 and P3. A third group of 11 mice received a dose of saline only on P1 and P3. A fourth group of 15 mice received a single subcutaneous dose of 400 ug/g of an antisense oligonucleotide ISIS 813208 (ASO) on post-natal day 1 and a second dose of 400 ug/g ASO on post-natal day 3 along with doses of saline on days P1 and P3. A group of 8 untreated wild-type mice were also used as a control. A fifth group of 12 SMA mice received a single subcutaneous dose of 400 ug/g of an antisense oligonucleotide ISIS 813208 (ASO) on post-natal day 1 and a second dose of 400 ug/g ASO on post-natal day 3along with a dose of saline on days P1 and P3. After each group of mice was treated, the mice were observed for Survival, body weight, time to right and time to fall. Without treatment, SMA mice typically do not live longer than 20 days. An "n/a" label in the table below indicates that the SMA mice had died. This example demonstrates that combination treatment of SMA mice with an antisense oligonucleotide targeted to SMN-NAT and an antisense oligonucleotide targeted to SMN increase mouse survival and body weight compared to SMA mice treated with only an antisense oligonucleotide targeted to SMN-NAT or only an antisense oligonucleotide targeted to SMN. Additionally, 4 out of the 15 mice treated with 449323+813208 survived for more than 120 days.

TABLE 15

| Median Survival and Average Body Weight | | | | |
|---|---|---|---|---|
| | Mouse Survival and Body Weight | | | |
| Isis No. | Median Survival | Average Body Weight at 20 days | Average Body Weight at 30 days | Average Body Weight at 40 days |
| WT Untreated | >200 d | 7.3 g | 11.8 g | 13.7 g |
| Saline + Saline | 18 d | n/a | n/a | n/a |
| 813208 + Saline | 18 d | n/a | n/a | n/a |
| 449323 + Saline | 25 d | 3.2 g | 4.6 g | 4.2 g |
| 449323 + 813208 | 37 d | 4.3 g | 5.2 g | 9.0 g |

What is claimed:

1. A method of increasing the amount of full length SMN2 mRNA in a cell comprising contacting the cell with a first antisense compound complementary to SMN-NAT nucleic acid and a second antisense compound complementary to SMN2 pre-mRNA;

wherein the first antisense compound comprises an oligonucleotide consisting of 12 to 30 linked nucleosides, and wherein the oligonucleotide is at least 85% complementary to an SMN-NAT nucleic acid sequence;

wherein the second antisense compound comprises an oligonucleotide consisting of 12 to 30 linked nucleosides, and wherein the oligonucleotide is at least 85% complementary to an SMN2 pre-mRNA; and wherein the SMN-NAT nucleic acid has a nucleobase sequence at least 85% identical to SEQ ID NO: 1 and the SMN2 pre-mRNA has a nucleobase sequence at least 85% identical to SEQ ID NO: 2.

2. The method of claim 1, wherein the first antisense compound is at least 85% complementary to SEQ ID NO: 1.

3. The method of claim 1, wherein the second antisense compound is at least 85% complementary to SEQ ID NO: 2.

4. The method of claim 1, wherein the first antisense compound complementary to SMN-NAT nucleic acid is a single-stranded oligonucleotide and/or the second antisense compound complementary to SMN2 pre-mRNA is a single-stranded oligonucleotide.

5. The method of claim 2, wherein the oligonucleotide complementary to SMN-NAT nucleic acid has a nucleobase sequence comprising at least 12 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

6. The method of claim 2, wherein the oligonucleotide complementary to SMN-NAT nucleic acid comprises at least one modified internucleoside linkage.

7. The method of claim 6, wherein at least one modified internucleoside linkage is a phosphorothioate internucleoside linkage.

8. The method of claim 2, wherein each internucleoside linkage of the oligonucleotide complementary to SMN-NAT nucleic acid is either a phosphorothioate internucleoside linkage or a phosphodiester internucleoside linkage.

9. The method of claim 2, wherein at least one nucleoside of the oligonucleotide complementary to SMN-NAT nucleic acid comprises a modified sugar.

10. The method of claim 2, wherein the oligonucleotide complementary to SMN-NAT nucleic acid has:

a gap segment consisting of ten linked deoxynucleosides;

a 5' wing segment consisting of five linked nucleosides; and a 3' wing segment consisting of five linked nucleosides;

wherein the gap segment is positioned between the 5' wing segment and the 3' wing segment and wherein each nucleoside of each wing segment comprises a modified sugar.

11. The method of claim 10, wherein the modified sugar is a 2'-O-methoxyethyl modified sugar.

12. The method of claim 3, wherein the oligonucleotide complementary to SMN2 pre-mRNA has a nucleobase sequence comprising at least 12 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

13. The method of claim 3, wherein each nucleoside of the oligonucleotide complementary to SMN2 pre-mRNA comprises a modified sugar.

14. The method of claim 13, wherein the modified sugar is a 2'-O-methoxyethyl modified sugar.

15. The method of claim 3, wherein the oligonucleotide complementary to SMN2 pre-mRNA comprises at least one modified internucleoside linkage.

16. The method of claim 15, wherein at least one modified internucleoside linkage is a phosphorothioate internucleoside linkage.

17. The method of claim 15, wherein each internucleoside linkage of the oligonucleotide complementary to SMN2 pre-mRNA is either a phosphorothioate internucleoside linkage or a phosphodiester internucleoside linkage.

18. The method of claim 1, wherein the cell is in a subject.

19. The method of claim 18, wherein the subject is a human having type I, type II, type III, or type IV SMA.

20. A method of treating a subject having SMA, comprising administering to the subject a composition comprising a first antisense compound complementary to SMN-NAT nucleic acid and a second antisense compound complementary to SMN2 pre-mRNA;

wherein the first antisense compound comprises an oligonucleotide consisting of 12 to 30 linked nucleosides, and wherein the oligonucleotide is at least 85% complementary to an SMN-NAT nucleic acid sequence;

wherein the second antisense compound comprises an oligonucleotide consisting of 12 to 30 linked nucleosides, and wherein the oligonucleotide is at least 85% complementary to an SMN2 pre-mRNA; and wherein the SMN-NAT nucleic acid has a nucleobase sequence at least 85% identical to SEQ ID NO: 1 and the SMN2 pre-mRNA has a nucleobase sequence at least 85% identical to SEQ ID NO: 2.

21. The method of claim 20, wherein the first antisense compound is at least 85% complementary to SEQ ID NO: 1.

22. The method of claim 20, wherein the second antisense compound is at least 85% complementary to SEQ ID NO: 2.

23. The method of claim 20, wherein the first antisense compound complementary to SMN-NAT nucleic acid is a single-stranded oligonucleotide and/or the second antisense compound complementary to SMN2 pre-mRNA is a single-stranded oligonucleotide.

24. The method of claim 20, wherein the oligonucleotide complementary to SMN-NAT nucleic acid has a nucleobase sequence comprising at least 12 contiguous nucleobases of any of the nucleobase sequences of SEQ ID NOs: 4, 8, 9, 10, 14, 18, 20, 21, 22, 23, 25, 26, 29, 32, 33, 35, 36, 40, 41, 42, 44, 45, 46, 52, 54, 57, 58, 59, 60, 63, 64, 65, 66, 67, 68, 69, 72, or 77.

25. The method of claim 20, wherein the oligonucleotide complementary to SMN-NAT nucleic acid comprises at least one modified internucleoside linkage.

26. The method of claim 20, wherein at least one modified internucleoside linkage is a phosphorothioate internucleoside linkage.

27. The method of claim 26, wherein each internucleoside linkage of the oligonucleotide complementary to SMN-NAT nucleic acid is either a phosphorothioate internucleoside linkage or a phosphodiester internucleoside linkage.

28. The method of claim 20, wherein at least one nucleoside of the oligonucleotide complementary to SMN-NAT nucleic acid comprises a modified sugar.

29. The method of claim 20, wherein the oligonucleotide complementary to SMN-NAT nucleic acid has:

a gap segment consisting of ten linked deoxynucleosides;

a 5' wing segment consisting of five linked nucleosides; and a 3' wing segment consisting of five linked nucleosides;

wherein the gap segment is positioned between the 5' wing segment and the 3' wing segment and wherein each nucleoside of each wing segment comprises a modified sugar.

30. The method of claim 28, wherein the modified sugar is a 2'-O-methoxyethyl modified sugar.

31. The method of claim 20, wherein the oligonucleotide complementary to SMN2 pre-mRNA has a nucleobase sequence comprising at least 12 contiguous nucleobases of any of the nucleobase sequences of SEQ ID NOs: 81, 82, 83, 84, 85, 86, 87, 88, 89, 90, 91, 92, 93, 94, 95, 96, 97, 98, 99, 100, 101, 102, 103, or 104.

32. The method of claim 20, wherein each nucleoside of the oligonucleotide complementary to SMN2 pre-mRNA comprises a modified sugar.

33. The method of claim 32, wherein the modified sugar is a 2'-O-methoxyethyl modified sugar.

34. The method of claim 20, wherein the oligonucleotide complementary to SMN2 pre-mRNA comprises at least one modified internucleoside linkage.

35. The method of claim 34, wherein at least one modified internucleoside linkage is a phosphorothioate internucleoside linkage.

36. The method of claim 34, wherein each internucleoside linkage of the oligonucleotide complementary to SMN2 pre-mRNA is either a phosphorothioate internucleoside linkage or a phosphodiester internucleoside linkage.

37. The method of claim 20, wherein the SMA is type I, type II, type III, or type IV SMA.

* * * * *

SEQUENCE LISTING

```
<160> NUMBER OF SEQ ID NOS: 104

<210> SEQ ID NO 1
<211> LENGTH: 1613
<212> TYPE: DNA
<213> ORGANISM: Homo sapiens

<400> SEQUENCE: 1

agtaattaaa agtgtagtac tgacatcaat atacactaat agacaatgta acagaattga      60

gagtcagaaa tagccctgtg atatatgtga ctgattttaa ctaaagttac aaatgtggtt     120

taatagagaa agcatagtag tttcaagaaa tggtggtaaa actattggaa atccttatgc     180

aaaaacaaac caaatttcca cctacactga gccacatata agaattaata caaaatggat     240
```

```
tacagaccta agtgtaaaac taaaactcta aactgtgtaa aaaaaaaaaa gagagaaaaa    300

tctgtgatca tggattgcct ataacaaaag aacaaactga aatggccttg ttgcctgggg    360

tggcacccga ggttcttggt ctcacgctga ggaaatcaag gacgctgaca caccaagggt    420

gtgaggctag agcagaagtt taataggcaa aagaaagaga ctagctctct cctgcagaga    480

gaggtcctga aaagagttcc cattccacag tgaaatgcaa gcatttttat aaatgagcta    540

atgggaaggg ggtagcttat ctacacatag ggagcaaaaa accagttagg accaggtgtt    600

gccatctgca cagagcgtga atctctggca tcccccaccc caacctttta ttatgcaggc    660

aggtccttgg cctgagctac tccacattgc ttatctcttt cctattgtgc atgtgctaaa    720

taaggggagg tggagccacc atggtggaca tgcctggccc caggtacccc tttctctccg    780

tgcagctgca ggcaacccca acaactcaca acatgcaagc ttccagcttc cttatctgag    840

tatgtactaa ggtccactgt gtttacttca catactgtgt ttacttcaca tacccacctt    900

acgtatgtga agcttgctga ttacccagga agctcccccct ctgtgccaga gctgcttcct    960

tatacatgtt tacagcccga tcttccaggc tgctccttgt tagaagagaa gtgatttctt   1020

gggctgcttt ttgttagaag ggaagttcta ccgaggactc tgtctaacta tcggcttacc   1080

tagtcttttt ttacctcctc tctcaaaacc atcaaagaaa aaactgaaaa attagatttc   1140

agcaaaatta agattttctg ttcttaaaaa gacgttgtta acaaaatgaa aaaccaaagt   1200

gtaaaccggg agaaaataca tgcaagttac ctatctgata aagatattgt acccagcaaa   1260

catgaagaac tctcaaacct caacaacaaa aaaattcaat taaaagatgg gtaagttggc   1320

cgggtgcagt ggctcatact tgcaatccca atctttggga ggctgaggca ggaagattgc   1380

ttgagcccag gagttcacga caagcccagg caacataatg agaccttgtt tctacaaaat   1440

tttaaaaaat tagccaggca ttgtggcgtg tgctcgtaat ttcagctact cagaaggctg   1500

agacaagaag actgagcgca ggaggtggag gctgcagtag gctgtgtgat tgcaccactg   1560

cacaacagcc tgggtgacag agtgagacac tgtctccaaa aaaaaaaaaa aaa          1613
```

<210> SEQ ID NO 2
<211> LENGTH: 28070
<212> TYPE: DNA
<213> ORGANISM: Homo sapiens

<400> SEQUENCE: 2

```
ccacaaatgt gggagggcga taaccactcg tagaaagcgt gagaagttac tacaagcggt     60

cctcccggcc accgtactgt tccgctccca gaagccccgg gcggcggaag tcgtcactct    120

taagaaggga cggggcccca cgctgcgcac ccgcgggttt gctatggcga tgagcagcgg    180

cggcagtggt ggcggcgtcc cggagcagga ggattccgtg ctgttccggc gcggcacagg    240

ccaggtgagg tcgcagccag tgcagtctcc ctattagcgc tctcagcacc cttcttccgg    300

cccaactctc cttccgcagc ctcgggacag catcaagtcg atccgctcac tggagttgtg    360

gtccgcgttt ttctacgtct tttcccactc cgttccctgc gaaccacatc cgcaagctcc    420

ttcctcgagc agtttgggct ccttgatagc gttgagtgga ggccctgccg cgacttggca    480

gtagcttatt ttgttcactc ctctctggct ggtgtggggg aggtgggggc attaggccag    540

ggtgaagcag gggaaccact taggagtctg ttaagatgat ctgaacttca gaacaagatg    600

ttattaacag agtgaaagta tttggattct gggtatattt tgaaatcgga ggcaacaggt    660

ttttcagata gattcgataa cggaggttat cctgaatagt tgaaaagata aagttgcctt    720

ttgctgaggt gggaaagaga agattgccag tagagcaggt ttctcaggag ttcagtcttg    780
```

```
ggcatagcat ggtaggggtg aatttggctg gagtgagttg gagagtagga gaagagaaat    840
ccaaggcaac atttgaccag cctgggcaac atagtgtgac tccgagtctg caaaaattag    900
acgggtgttg tggtgcgcgt ctgtggtctc agctacctgg aaggttcagg ccttggaagg    960
ctcagggagg tggaggctgc agtgatctgt gattgcgcct ctgcactcca gcctgggcga   1020
cagagccaga ccctgtctta aaacaaaata aacggccggg cgcggtggct caagcctgta   1080
atcccagcac tttgggaggc cgaggcggcc ggatcacaag gtcaggagat cgagaccatc   1140
ctggctaaca cggtgaaacc ccgtctctac tacaaataca aaaaattagc cgggcgtggt   1200
gacgggcgcc tgtagtccca gctactcggg aggctgaggc aggagaatgt catgaagccg   1260
ggaggcggag cttgcagtga gccgagatcg cgccactgca ctccagcctg ggcgatagag   1320
caagactccg tctcaaataa ataaataaat aaataaataa ataataaaaa catcggtagg   1380
catatttcaa ggaattctat ttaaaaaaaa ttttttttaga gacaagttcg ctctctgtgg   1440
cccaggctgg agtacagtgg catgatccta gcccatggca gcgttgatct cttggcctca   1500
agcgaccctc ctttggagtc gctgggccta aaggagtgag ccaccacgaa attttattat   1560
aaatggaggg tagagaaatt gggcaataaa tggaggggga agtgagttaa gaggaatttt   1620
aattatgtgt gtgtggtttt aaaagagggg ggtcttgctc tgttgcccag gctgctgggg   1680
tgccagtggc gcaatcatga atcactacag ccttggactc ctggcctcaa gctatcctcc   1740
cacctctgcc tcccaaagta ctgggattac tagtgtgagc cactgcacta agataggagc   1800
aacatgtttc agcatgtttg tgggttgata ggaaagatga gaatgggaaa gttgatgtcg   1860
gaaagaagac aatggctaga gcaatgtcct agagtaggta agaagggatg gatttggcct   1920
ttgttggaaa cattagcggt tcttttggtg acagctatat agttaacaca tctatgatac   1980
gtgaatgggc agataggatg gcaggagatt ttgaaagttc tcttgattct tactgttctc   2040
ttagtgaaag aagcaaggtt atcagctaga agctgggatg ggagaggaaa gagaagatgg   2100
gaagtagata gttctttaga agagtgggca agggttggac tagggaagtt tagtggaaat   2160
attgctaggc aacataaaga gcctacttga gattcgtggt catgagttga aggagaccag   2220
acagcaagat tgtgtatgag ggcacccaca gagtaaatgg agagttgaaa ttaatgcagt   2280
tgtgatttta ccacgtggat atgaagaagt gagggggaga agtacaaagg agttctctta   2340
atgattgacc atggaattta agctggctaa gaaaggaagt gagaggccgg gcgcggtggc   2400
tcacgcctgt aatcccagca ctttgggaga ctgaggtggg tggattacct gaggtcagga   2460
gtttgagacc aacctggccg atatggcgaa accccatctc taataaaaat acagaaaaat   2520
tagccgggaa tggtggcagg tgcctgtaat cccagctact caagaggctg tggcaggagt   2580
atcccttgga cccaggaggt ggaggttgca gtgagccgag atcacgccac tgtactccag   2640
cctggacgat atagtgagac ttcacctcaa aaaaaaaaaa aaagaaagga agtgaggatt   2700
ttaagaccct gagagacagt ttaaaaagtg ggaggatcgg ccgggcgctg tggctgacac   2760
ctgtaatccc agcactttgg gaggccgagt tgggcagatc acaaggtcag gagttcgaga   2820
ccagcctggc caatatggtg aaaccttgtc tctactaaaa atacaaaaat tagccgggca   2880
tggtgtcacg tgtctataat cccagctact cgggaggctg aggcagaaaa attgcttgaa   2940
cctgggaggc agaggttgca gacagctgag atcactccat tgcactccag cctgggcaac   3000
aagagcaaaa ctttgtcttt aaaaaaaaaa aaaaaaaaag aatacaaaaa ttagccgggc   3060
gtggtggcgc gtgcctataa tcccagctac ttgggaggct gaggcaggag aatcagttga   3120
```

-continued

```
acacgggagg cgaggtttgc agtgagccga gattgcgcca ctgcactcca gcctgggcga   3180
cagagcagga ctcctcttgg aaaaaaaaaa ttagctgggc atggtggcag gtgcctgtag   3240
tctcagctac tagggaggct gaggcaggaa aatcacttga acccgggatg tggagtttgc   3300
agtgacccga gatcgtgcca ctgtactcca tcctgggcga caaaatgaga ctctgcctca   3360
aaaaaaaaaa aaaaaaaaag tgggaggatc aatgtactgc cagtcctaat gaagtggaat   3420
gattgtcccc atcaaatcac tagtaggagt aagttgcaga gcctagaagg tgatggttaa   3480
gagagtggga ttcttgaaac tgcatttatg gagaggttgt ggttattggt tataataaat   3540
aaatacagtt gaagtgagtg agtagctgag atttggggat gtatcagttc attcttacac   3600
tgctacaaag acatacctga gaccaggtat ttataaagat aagaggttta atcagctcac   3660
agttctgctg cctgtacagg cttctcttgt ggaggcctaa ggaaacttac agtcatggtg   3720
gaaggtgaag gggaaacaag cacagtcttc acatggccag caggagagag agagaagggg   3780
gaagtgctac atactttaaa acaaccagat cttgtgagaa cgcttatcag gaaacagcac   3840
ttggggatgg tgctaaatca ttagaaatca cccccatgat ccagtcgcct cctaccatgc   3900
ccacctccaa cactggggat cacaattcag catgagattt gggtaggaac acagagctgc   3960
accacatcag aggatgtaca agattgtggt ggagaggagt ttagagacct gcaaatatag   4020
ggtaattgaa gggatcatct acatggatat ttaaatcacc aaaaattatg acaggagtag   4080
tgttggagag agaactgcga tgtaaacatt aaggaatgag gaagagtgac tcggtaggct   4140
gtaggtgact gcaataggaa acgataatag actgtgagtc tggtgacaag attttccttc   4200
tttctttttt tccccccccc cgagacaggg cctctttttg ttgcccaggt gggagtgcag   4260
tggcgcgatc acggctcact acaacctcct cccaagctca agggattctc ccacttcagc   4320
ctctcaagta gctggaacta caggtgctga ccaccatgcc tggctacttt ttgtcaggat   4380
tttcaaggct gggaattttg agaggggaat ggaggagaat aatctgaaag tgcaagtaag   4440
gagcagggaa gatttctttt ttcttttttt tttttttttt tgagtcggag tctggctcag   4500
tcgcccaggc tggagtgcag tggcgagatc tccgctcact gcaagctccg cctcccgtgt   4560
tcacgccatt ctcctccttc agcctcccga gtagctggga ctacaggcgc ccgccaccac   4620
gcccagctaa ttgttttttt gtatttttag tagagacggg gtttcaccgt gttagccagg   4680
atggtctcaa tctcctgact ttgtgatccg cccaccccgg cctcccaaag cgcttgggat   4740
tacaggcgtg agccaccgcg ccagccagag cagggaagat ttcttcccca catctccagt   4800
aggtacagtg atatgaagtg tgtggaggag aaaagaggaa acatctatca tttgagatgg   4860
ctgcgaaagg aaaaggcatc ctcagggagc tagattttac ttagagcaag aaatgaaggg   4920
atgattcaga ggttaaaaga gtggatttta tgaattactc aagggagcac agtggaagtt   4980
tcaggaagtg gtaggagaag gtagaagatg gcagggtgtt gggaataatt tgagaaatct   5040
gagctactgg aaatgactga gaatcagata taaaggcagt cctggtggtc cgttctggct   5100
gccgttgctg tgtaacgaat ctgccaaaac ttagtggctt gaaacaacaa agaacatttt   5160
attatctctc attgtttctg tgggttagga atttgtgaga gccgtgctgg gcagttttcg   5220
tgcggctgtc tcgtggttgc acctacatag ttgctagagc tacagtagct ggggactgag   5280
cagctaggga ttggcaggct atctcttttt ttcatgtagt ctcatgaaga tttctttatg   5340
tggtttcaat gtgtgggctg gtttggattt ccttatagca tggtggcctc agttggattg   5400
ctgttttgtg atccttttca tccctccttg tcctgtcccc agacaaccac tgatctactt   5460
tctgtcacca tagattagcc tgcattttta agaattttta taaacgtgga atgatagagt   5520
```

```
accttttttg tcacgtttct tttatttatc atagctattt tgattttcat ccattttatt   5580
gctgagtagt atcccattgc atgtatatac tatactgtat tcattcgctt gcttgtgaac   5640
atttgggctt tttccagttt gggactgtta acaagtagag ccactatgaa tattagtgta   5700
taagacttca tatagccaag gctggcagat cgcttgagcc caggagtttg agaccagcct   5760
gggaaacatg gtgaaacctc tattttttatt ttaaaatcaa aaattaaaaa ttttctataa   5820
aaaattttaa agaagacttt gtatagacat acgctttcat ttttcttgag tgaatactta   5880
ggtctcaggg tagatgtatt ttaagtcttt aaggagctgt caaactcttc ctcaaagtgg   5940
tggttgtacc atgttacttt ttaatataac agagattaat tgagcaaaga aaaattcaaa   6000
agttggacag cccccacaac taaataggtt cagaacagct cccccatttt gcattttgac   6060
cagcaatgta tgaaagttcc atttgctcag tgtccctgca aacacctggt atggtcagtc   6120
tttttaattt taggcattat aatagatata gtggcttctt gtgattttaa ttagcatttc   6180
ctaatgacca gtgctgctgt tgatcatttc atgagtgtat ttgccatccg tatatctttt   6240
ttggtgaagt gtctattcaa atcatttggg tttttttttt ttttgttttt ttttttttgga   6300
gacagtgtct cactctgtca cccaggctgt tgtgcagtgg tgcaatcaca cagcctactg   6360
cagcctccac ctcctgcgct cagtcttctt gtctcagcct tctgagtagc tgaaattacg   6420
agcacacgcc acaatgcctg gctaattttt taaaattttg tagaaacaag gtctcattat   6480
gttgcctggg cttgtcgtga actcctgggc tcaagcaatc ttcctgcctc agcctcccaa   6540
agattgggat tgcaagtatg agccactgca cccggccaac ttacccatct tttaattgaa   6600
tttttttgtt gttgaggttt gagagttctt catgtttgct gggtacaata tctttatcag   6660
ataggtaact tgcatgtatt ttctcccggt ttacactttg gtttttcatt ttgttaacaa   6720
cgtcttttta agaacagaaa atcttaattt tgctgaaatc taatttttca gtttttttctt   6780
tgatggtttt gagagaggag gtaaaaaaag actaggtaag ccgatagtta gacagagtcc   6840
tcggtagaac ttcccttcta acaaaaagca gcccaagaaa tcacttctct tctaacaagg   6900
agcagcctgg aagatcgggc tgtaaacatg tataaggaag cagctctggc acagaggggg   6960
agcttcctgg gtaatcagca agcttcacat acgtaaggtg ggtatgtgaa gtaaacacag   7020
tatgtgaagt aaacacagtg gaccttagta catactcaga taaggaagct ggaagcttgc   7080
atgttgtgag ttgttggggt tgcctgcagc tgcacggaga gaaaggggta cctggggcca   7140
ggcatgtcca ccatggtggc tccacctccc cttatttagc acatgcacaa taggaaagag   7200
ataagcaatg tggagtagct caggccaagg acctgcctgc ataataaaag gttggggtgg   7260
gggatgccag agattcacgc tctgtgcaga tggcaacacc tggtcctaac tggttttttg   7320
ctccctatgt gtagataagc taccccttc ccattagctc atttataaaa atgcttgcat   7380
ttcactgtgg aatgggaact cttttcagga cctctctctg caggagagag ctagtctctt   7440
tcttttgcct attaaacttc tgctctagcc tcacaccctt ggtgtgtcag cgtccttgat   7500
ttcctcagcg tgagaccaag aacctcgggt gccaccccag gcaacaaggc catttcagtt   7560
tgttcttttg ttataggcaa tccatgatca cagatttttc tctcttttttt tttttttacac   7620
agtttagagt tttagtttta cacttaggtc tgtaatccat tttgtattaa ttcttatatg   7680
tggctcagtg taggtggaaa tttggtttgt ttttgcataa ggatttccaa tagttttacc   7740
accatttctt gaaactacta tgctttctct attaaaccac atttgtaact ttagttaaaa   7800
tcagtcacat atatcacagg gctatttctg actctcaatt ctgttacatt gtctattagt   7860
```

-continued

```
gtatattgat gtcagtacta cacttttaat tactattgct tcagggtatg tcttgtaaac   7920
caaaaataaa attataggcc ccccccgccc ctgcacaacc aactgaatgg acccatcctc   7980
tcagccaagg gcattccaaa attaacctga aaaactagtt caagccatga tgggaagggg   8040
gagttggaca tgtctcatca caccctacta ccttttggaa ttactgatag aacagactct   8100
taaagtctga aaagaaacat ttacaaccta ccctctctga agcctgctac ctgggagctt   8160
catctgcatg ataaaacctt ggtctccaca accccttatg gtaacccaaa cattcctttc   8220
tgttgataat aactctttca actagttgcc aattagaaaa tctttaaatc ttcctatgac   8280
ctagaaacct ccctaccccc actttgagtt gtcctgcctt tcctgacaga actcatgtac   8340
atcttacata tattgattga tgcctcatgt ctccctaaaa tgtataaaac aaagctgtac   8400
cccaccacct tggggacatg tcatcaggac ctcctgtggc tgtgtcatag gagcgtcttt   8460
aactttggca aaataaactt tctaaattga ttgaaacctg tcttagctac ttctggttta   8520
cagtcttaaa gttagataat gtaaattgtc cagctttggt ttatttttgt ccttagtagt   8580
tccatataaa ttttagaatc agcttttcaa tttaatacac tactttcctc ttagatccac   8640
aattaaatat atttgatgct aacaattctg ttttatgttt ttcgtttttt tttttgaga   8700
caagagtttc gctcttgttg cccaggctgg agtgcagtgg cgcgatcttg gctcaccaca   8760
acctccacct cccaggttca agcaattctt ctgcctcagc ctcccgagta gctgggatta   8820
caggcatgcg ccaccacgcc cggctaattt tgtattttta gtagagacgg ggtttcacca   8880
tgttgatcag gctggtcttg aactcctgac ctcaggtgat ccacccacct cggcctccca   8940
aagtgttggg attacaggcg tgaaccacca tgcctggcca gttctgttat ttttaaaacc   9000
caagtttccc tggtcatatc ttggttggat gaagcgtatt ttcaatagat taccctggaa   9060
aggctagtga gtacggtatt cttctacatt ttagactttt cttagtcttg ctacttcaag   9120
gacagctagg ctgcatataa aattcttggc tcatactttt tccccataaa tttctatgag   9180
aaagtctaat gataactgat tttctttatt ttgtaactta gtctttttgc ttagaggctc   9240
tctgaggatg ggaggggggtt cttcctccca tccctaggaa tttttctttt ttttaaattc   9300
ctaatcacta gaccaccagg aagattgttt gttttgtttt gtttttattc ttcagggacc   9360
ccatttatac atacgttaaa taaatactgt ttgccaatgt atcaaccatt ttgcttctta   9420
tttattttttg ttcctttggt tctttttcat ggctttgctt tggtgctcct tagattttca   9480
gtcagatgta tttgtccttg ggtaccttgt aatcagtatt accttttctt ctgtcgcttt   9540
gttttctgtt cgttttgaaa ttacttgttt cctggtctgg caataacagt tgagatatga   9600
ggagtttgag ctgccatctg tctatgtatc ttgctttaag actgcactct tctattgata   9660
tcactggcct tgattttgtg atttctttat ttcttcagga ccacccttca ttttctactg   9720
tttgcttcct tttttttga gatggagtct cactctgtca ctcaggctgg agtgcagtga   9780
tcttggctca ttgcaacctc tgcctcccgg gttccagcaa ttctcctgcc tcagcctccc   9840
aagtatctgg gactacaggt gtgcaccacc atgcccggct aagttttgta tttttaatag   9900
agacggggtt ttgccacatt ggcaggctgg tctcaaactc ctgatgtcaa gtgatccacc   9960
caccccaccc acctctgcat cccaaagtgc tgggattaca ggaatgagct gccgtgccca  10020
gcctcccccc taccccccctt tttttctttc gagacagaga ttataggtgt gagccactgg  10080
acccagcctg tttttattcc ttttaccaaa tctccaagga atatcttccc ttccaagtgc  10140
gaatgtaacc ttaagtcagt taacctcttt gtgattactt ttcttatctg caaagtgact  10200
taatgatctt aagtactttt tttttttgag acagggtctc actgtcaccc tggctggagt  10260
```

gcagtggcac gatctctgat ctccactcac tgcaatctcc tcttccctgg ttcaagcggc 10320
cctcccacct tagccttctg ggtagctggg actacagatg tgaaccacca cgcccagcta 10380
atttttgtac tttttgtaga gatggggttt tgccatgttg cccaggctgg gattattaag 10440
tactttttat catacagcaa gattgacatt ttatattgga atacatttgt ctctatataa 10500
cggagattaa caggaaaatg acaagcctgg gtgcggtggc tcatgcctgt aatcccagca 10560
ctttgggagg ctgaggtggg aggatcactt gaggtcagga gttcgagacc agttttgcca 10620
agatgatgaa agcccatgtc tactaaaaat acaaaaatta gcccagcttg atggtgggcg 10680
cctataatcc cagctatttg agagactgag gcaggagaat cacttgaacc tgggcagcag 10740
aggttgcagt gagccgagat catgccactg cactccagcc tgggtggcat agcgagactc 10800
ttgtctcaag agaaaacaaa acaaaacaaa aaaaaaacag gaaaatgaca aaaagtaata 10860
ttacaactca gtgaatttta taacaaactt ttttggaatt cattgactaa tactatacca 10920
aatccaaaat actctctagt ataccaaatc caactctacc ctatagtata aattggattc 10980
tatttggact tgtctcacta atccctcata cagtgtgttt tattttttat tgaagtaaaa 11040
aaatttgtca ttttaaccat ttttaagtat atagttcagt aatattaagt atgttcatgt 11100
tgttgcgcaa tagatcttcg gaagtttttc gtcttgcaac ctgaaactct acccattagc 11160
aaattcccat ttctccttac acttagccct tggtaatcat cattcttttt tttttttttt 11220
tgagatggag ttttactctt gttgcccagg ctggagtgca atggtgcaat ctcgactcac 11280
cacaacctcc gcctcccagg ttcaagcaat tctacctcag cctcccgagt agctgggatt 11340
acagtcatgc accaccacgc ccggctaatt ttgtattttt agtagagaag ggggtttctcc 11400
atgttgaggc tggtctcgaa ctcctgacct caggtgatct gcccacctcg gcctcccaaa 11460
gtgctgggat tacaggcgtg agccactgcg cctggcccat tctttctaat tctataaatt 11520
tgactactta gttaccttac ataaataaat tcttatagtt agtgttattt ttgcttccat 11580
gccttttttg ttgttgttca tgctcttact tggaatgcgt tctattttgt ctacctatgc 11640
acatcctgtt gggttttttt tttttttggg ggtttttttt gttttttttt gttttttttt 11700
cccagacaag gtctcaattt gttacccagg ctggagtgca gcggcgccat ctccactcac 11760
tgcatcctca acttcctggg cccaggtgat cctctcgcct cagcccctgc aggtagctgg 11820
gactataggc atgtgccacc atgcccagct aaatttggtt tttttgtttg tttgtttttg 11880
agacagagtc tcactctgtc acccaggctg gagtgcagtg gcacaatctc agctcactgc 11940
aatctctgcc gcccgggttc aagtgattct cctgcctcag cctcccaagc agctgggatt 12000
acaggtgact gccaccacgc cagctaagtt ttgtagtttt agtagagatg gggtttcacc 12060
ttgttggcca tgctggtctc gaactcctga cctcgtgatc tgcctgcttc tgcctcccaa 12120
agtgctggaa ttacaggcat gagccaccac gcccggccag aatttttgta tttttagtag 12180
acacaaggtt cttaccctgt tgcctaggct ggtctggaag tcctggactc aagcaattca 12240
cctgccttgg cctcccaaaa tgctgggatt acaagccacc atgcccggcc taaatcctgt 12300
tgttttgttt tgttttattt tgttttgttt tgttttgttt gtttttgag acagagtctc 12360
gctatgtctc tcaggctgta gtgcagtggc gcgatcttgg ctcactgcca cctctgcctc 12420
ccaggttcaa gtgattctcc tgcctcagcc tcccaagtag ctgggattac aggcatgtgc 12480
tactatgtcc ggctaatttt tgtattttta gtagagacag ggtttcacca tgttggccag 12540
gctggtctcg aactcctgac ctcgtgatcc acccacctcg gccacccaaa gtgctgggat 12600

-continued

```
tacaggcgtg agtggttttt atttcttagg ccggtttcct ccatatgatc ttgcagtaga  12660
cattaatttc tttcctttt aattaaaata ctgtttgtat ttcacatttt gatgtttgtt  12720
aagatttgtt ttatattgtt ttttgttttg tcttgtgtga tagtcttaaa tccctagtta  12780
gataataact ggagagtacc atgtttctat atatctctca gtgacttgca cagtgctagc  12840
agatagtgct aaaaaattat ttattattat tattattttg ttattgttgt tgttgttgtt  12900
agacagggtc ttcctctgtc acccaggcta gagggcaatg ggatgatcat agcttactgc  12960
agcctccaac aactgggctc atgtaattct cctgcctcag cttcccaagt agctgggatt  13020
acaggcatga gccaccatgt ctggacaaaa atatttccag gtgcagtggc tcatgcctgt  13080
aattcccaca cttgggaggc cgagcgaggc tggaggatca cttgagccta ggagttcaag  13140
accagcttgg ctaagatggc gagaccccgt ccctacaaaa aattttaaaa actagccagg  13200
catggtggca tgcacctata ttcccaacta ctcagtgggc tgaggtggga gggtcatttg  13260
aacacaggaa tttgagggga gaaaaaaaga agagagaaag agaagtgaag gaaggaagaa  13320
aggaaggagg gagggagaga agaaagaaac gaaagaaagg aaaagaaaag gaaggaaaga  13380
aaattggtac caggaaagca ggaaagggaa atggaagtaa aaaaataata ataataataa  13440
aatgaaaatt ggttagtcac tattaacaat ttgtatcctt ataatctgga aacattataa  13500
tttcaaaaga aaaaatattc tttggatcat aggttctgag gtcagaacag cattcccgta  13560
gtctagatga agtcaagttt tatctgatct taattgaaat aaatatagct ggccttgaac  13620
aaatctactc atggtatgtg gataggaatt aaattgtagg ggcattcact tgatggcatt  13680
cattcttaga acatttacct atgtctagct tttggagtaa agtcacataa cctctaacca  13740
ggtaagtttc ctgtggcttt atttaggatt ttaaatactc attttcagtg taattttgtt  13800
atgtgtggat taagatgact cttggtacta acatacattt tctgattaaa cctatctgaa  13860
catgagttgt ttttatttct taccctttcc agagcgatga ttctgacatt tgggatgata  13920
cagcactgat aaaagcatat gataaagctg tggcttcatt taaggtatga aatgcttgct  13980
tagtcgtttt cttattttct cgttattcat ttggaaagga attgataaca tacgataaag  14040
tgttaaagta catgttattc agttttcatt ttgaagatta gatggtagta tgagttagtt  14100
aaatcaggtg atatcctcct ttagaagttg atagcctata tatgtcatcc tttgtggagg  14160
caatttaaat aaaatttaaa acatttattc ctggctgggt atggtggctc actcctgtaa  14220
tcccagcact ttgagaggct gaggcgggtg gatcacctga ggtcaggagt ttgagaccag  14280
cctggccaac atggtgaaac cccgtcttta ctaaaaatac aaaaattagc caagcatggt  14340
ggcacgtgcc tgtaatccca gctgcttggg acactgaggc aggagaattg cttgaacctg  14400
gggggcagag gttgcaatga ttgcaccact gcactccagc ctgggcgata gagtgagact  14460
ccatctcaga aaacgaacaa acaatgtatt ccttttagta tttttacatt gtatcaaact  14520
atggaagtcc tctaattgag attaataaga aaaagacaat ctgaattata attttaaaca  14580
tttaacaagc atgtagtaaa ataatgatga agataaatag cattagtaca gcaattaata  14640
tttgtagcat gctgacagtg ctctgtgtgc gtttcatata ttaaattact ctaatcatcc  14700
caaatcctgt aagttgggta tcaattcaag tgttcctatt gggtaggaat atacagttct  14760
tttaggaaat gtagtatggt tctgtgtctc aaacaggaca cttacacagt tggccaacat  14820
catcaccttc tccattctct gagatgttta gtcttactga gcactaaata tgggtcatca  14880
atagtccaga ctaccttgag caaacaatag tccagactac cttgagcaaa cagagcatat  14940
actcatacag tgtataaaga gcaccaagca tacagatttc atgtctttct catagttact  15000
```

cttgtaacat gagctaaaga tcagacctct atgtcacctt tgtaactgat ttctagattt 15060
ttttttttt ttgagatggg gtcttgccct gtcacccagg ctggagtgta gtggcgtgat 15120
catgcctcat tggagccttc aactcatgag ctcaaacaat cctcctacct cagcttcctg 15180
agtagttggg accacaggtg tgtgccacca cacccagctc atttttgtat tctttgtaga 15240
gatgcagtct caccctgttg cccacgctgg cctggaactc ctgagctcaa aagatccctc 15300
cgccttgacc ttccaaagtg ctgggattac aagcatgaac cactgcaccc ggcctagatt 15360
tttaaatgtg ctttccagta tacactgaaa ctagaagtcg actaaagaat taccaagaga 15420
attctataaa atagagattg aaatggggct cgatgtggga tgggttggtg atattgcagg 15480
gagaagtaat ctgagtaaag gaggaaaaga actgatttgg gaaaacgata gttttagtag 15540
tgagtttgag tatgaattaa gttgagattg aatttgaatt aagttgaggt tgaatatgaa 15600
ttaagttgag gttgagtttg aggtatgaat taagatgtga aattgatcat tggaaatgtt 15660
agattgagaa aagtcacagc tggattaata gcttcagaag tgtgtttgca gacagttgca 15720
actaaagtaa taagaataga tggccttggc cgggcgcggt ggctcacgcc tgtaatccca 15780
gtactttggg aggctgaggc gagcaaatca cgaggtcagg agttcaagac cagcctggcc 15840
cacatggtga aaccccgtct ttattaaaaa tacaaaaatt agctgtgcac agtggtgcac 15900
gcctgtaatc ccagctactc gggaggctga gacaggagaa tcgcttgaac ctgggaggtg 15960
gaggttgcag tgagctgaga tcagtgtgac tgcactccag cccggtgaca gagtgagact 16020
ctgtgtaaaa aaataaaata aataaaataa tggccgtaag caagtaaaga aggatggcca 16080
gctcttattg ggaatgccta aatctaaggc ttgatcagaa gtaatgaaac cgttggggcc 16140
ctacattgct atgacatcca aagggccatg aatatcagga agaaagataa ttaacagggt 16200
ctaatgttac agagaggttg agagcaagga gatttgatta aaagggtctt tagagctgat 16260
gtcaggtgta tgatgccttt aagagcagtt tttatagtgc agggggtggt caaaagagaa 16320
aataggtgct ttctgaggtg acggagcctt gagactagct tatagtagta actgggttat 16380
gtcgtgactt ttattctgtg caccaccctg taacatgtac atttttattc ctattttcgt 16440
agcatgctct aaagaatggt gacatttgtg aaacttcggg taaaccaaaa accacaccta 16500
aaagaaaacc tgctaagaag aataaaagcc aaaagaagaa tactgcagct tccttacaac 16560
aggttatttt aaaatgttga gatttaactt caaaggatgt ctcattagtc cttatttaat 16620
agtgtaaaat gtctttaact taagtgatta gtacagtgtt tctattgaca tatacttata 16680
caacttcaaa aacaactatt aaattttctg ttatttagga acatgcatat tagtcatgaa 16740
agtataaaga attagatggg aatgataaat gctaaaatca ggacatgtgt tccatttgtg 16800
aatggaaggc agggagaagg tgccgtttgg aaggagtacc caagagccgt aagctgaatt 16860
ggcagtgttt tacatcttaa gctgagagat agattttttt ttccccttt tctttaaaaa 16920
ctctaaaact gttaattcca aggaacccag aagtctaggt agattatttc tgctagttaa 16980
aagcagtagt cctgaaagct gaatattttg gtgtcttttg agccaacttt agtttcatca 17040
ttaccaaggg ggaagagagc taacagttga tgagcacttg ctctaggcca gtccagagtg 17100
ctgggcacca tacgcatttt atctccctcc cgctattcac aacaaatatg ggaggtagtt 17160
tatattatag ccatctaata agatggggaa actaagactc aaagagattc agaaacttgt 17220
ccatgattat aaatgtaaga gagttggaat tcagatttat gtatttagac cccaagcctt 17280
tctcattaca tcattttgcc ttccaaatct ctaccctcta tccttcacct ccccactgat 17340

```
caaaacgaga tgatagtttg ccctcttcaa aagaaatgtg tgcatgtata tatctttgat  17400
ttcttttgta gtggaaagtt ggggacaaat gttctgccat ttggtcagaa gacggttgca  17460
tttacccagc taccattgct tcaattgatt ttaagagaga aacctgtgtt gtggtttaca  17520
ctggatatgg aaatagagag gagcaaaatc tgtccgatct actttcccca atctgtgaag  17580
tagctaataa tatagaacaa aatgctcaag aggtaaggat acaaaaaaaa aaaaattcaa  17640
tttctggaag cagagactag atgagaaact gttaaacagt atacacagtt gtcagtttga  17700
tccaccgagg cattaatttt ttcttaatca caccccttata acaaaaacct gcatattttt  17760
tctttttaaa gaatgaaaat gaaagccaag tttcaacaga tgaaagtgag aactccaggt  17820
ctcctggaaa taaatcagat aacatcaagc ccaaatctgc tccatggaac tcttttctcc  17880
ctccaccacc ccccatgcca gggccaagac tgggaccagg aaaggtaaac cttctatgaa  17940
agttttccag aaaatagtta atgtcgggac atttaacctc tctgttaact aatttgtagc  18000
tctcccatga aacttttgta gcttaaatac acaagaattt tttgaaaagg aaataagata  18060
atgatgcaaa atagttaatt ttttaaaaaa atgttagaca ctgcagtgga tgcaacaaaa  18120
tactttatat gaaagattta tccagttaac ttttgtggag tattaggtat tagactaata  18180
attagcacac ttacttaagt tagaaagtat aataatgcgc cggacgcggt agctcacgcc  18240
tgtaatccca gcactttggg aggccaaggt gggcggatca caaggtcagg agatcgagac  18300
catcctggct aacacggtga aaccccatct ctactgaaaa tacaaaaaaa tttgccgggc  18360
gtgatggcgg gcacctgtag tcccagctac tcgggaggct gaggcaggag gatggtgtga  18420
accccggagg cagagcttgc agtgagtcaa gatcgtgcca ctgcactcca acctgggcga  18480
cagaatgaga ctccatctca aacaaaaaaa caaaacaaaa caaaaaaaag tgtaataata  18540
atttatcatt agctggatga tatgctgttg tttcccatgt cacctgtata agatatgtaa  18600
aataagaaca cattatttac atctaatata gataaaatcc tgaggcgctc tcagattgtt  18660
ttgtagagtt caaatgtaaa tattgttttc atttatggtc cttttggtta taagtaacag  18720
aaatcaactc taaaaagatt tttattatag gttagattat gtcatggaac cttaaggctt  18780
gtccctttct agttcttttg tgtaaagcgg tgatttcttc catggaggga atggtattta  18840
ggcaattttt tttttttttt cgagatggag tcttgctctg tcgctcaggc tggagtgcag  18900
tggcaccatt tcagctcact gcaacttcca cctcctgggt tcaagtgatt ctcctgcttc  18960
agcctcccaa gtagctgaga ttacaggcac ccgccaccac acccggctta ttttgtattt  19020
ttagtagaga tggggtttca ccatgttggc caggctggtc ttgaactcct gacctcaagt  19080
gatctcccca ccttggcctt ccaaagtgct aggattacag gcgcctagcc taggcagtca  19140
ttttcaaaaa acaagcatga ctcaccaaaa gttttaagat tttctgtgat aatgttctta  19200
ttgaggctta cattatatta cagtttcttg aatctaaaat gatgtaccct cttagaatat  19260
atacatcatg cttcattggt ctcagggggc tgatttttat aaggagagat ttgctagttt  19320
tcacaatatg tcctctaagt tggcatgtat agctaaacag gctttcataa aaatatacaa  19380
tttagttaat gaaatttggg atatagtctt ttatgattga aataattttg ctaaatagac  19440
tgtctctgat ttattaggta atcaccactc ttattttgtt ttacttcctt aatgtctaca  19500
tagaaaggaa atgagaaaaa tccagaggtt gtcatttgac ttatgagtct gtttgacttc  19560
aggatttggt acatgaaatt tcacttaatc tttttgatat gtataaaaca aatattctgg  19620
gtaattattt ttatcctttt ggttttgagt ccttttttatt cctatcatat tgaaattggt  19680
aagttaattt tcctttgaaa tattccttat agccaggtct aaaattcaat ggcccaccac  19740
```

```
cgccaccgcc accaccacca ccccacttac tatcatgctg gctgcctcca tttccttctg  19800
gaccaccagt aagtaaaaaa gagtataggt tagattttgc tttcacatac aatttgataa  19860
ttagcagaat agaggattgt aaaatgtcat tgtagaacat cccttgggcc agattctaat  19920
gggtagaaat ttgaactaaa cctctgggtt ttgtttgttt ttaatgcctt tctgttaccc  19980
agatgcagtg ctcttgtagt cccaagtcta agctctaggt tgccttcttt cctggcagaa  20040
gttggtgtct atgccataag gaggtagttc ctgttagaag ggatttaatt ataccttata  20100
taaggaatta gtgtttgccc ttctaggtat agttggatgt tagcttctga tgtaaactgg  20160
atttcttttt ctttctctct cttttttttt ttttgttttg gaggcagagt tttgcccttg  20220
taccccaggc tggagtgcag tggtgtgatc tcagctcaca gcaacctccg cctcctgggt  20280
tcaagcaatt ctgcctcggc ctcccaagta gctgggatta caggcgactg ccaccacacc  20340
cggctaattt ttgttttatt agtagagatg gggtttcacc atgttggcca gactgatctt  20400
gaactcctga cctcaggtga tccacccgcc ttggcctccc aaagcgctgg gattacaggc  20460
gtgagctgcc gcacccagct gtaaactgga tttctaatgg tagattttta ggtattaaca  20520
atagataaaa agatactttt tggcatactg tgtattggga tggggttaga acaggtgttc  20580
tacccaagac atttacttaa aatcgccctc gaaatgctat gtgagctgtg tgtgtgtgtg  20640
tgtgtgtgtg tgtattaagg aaaagcatga aagtatttat gcttgatttt ttttttttac  20700
tcatagcttc atagtggaac agatacatag tctaaatcaa aatgtttaaa ctttttatgt  20760
cacttgctgt cttttcgtcc tcgttaaatt taattttgtt ggtcttttgt tgttattggt  20820
tggttttctc caaatgctag ctatgttaag aaatttaagg ccaggtacag tggctcatgc  20880
ctgtaatccc ggcattttag aaggctgagg caggaggatc acttgagctc aggagtttga  20940
gaccagtctg ggcaacatag caagacctcg tctttgttta ggggaaaaaa aagaaattta  21000
agtaggagat tatataagca aaaatacaat taatttccag cattcactat ataatataaa  21060
tctccagact ttactttttt gtttactgga tataaacaat atctttttct gtctccagat  21120
aattccccca ccacctccca tatgtccaga ttctcttgat gatgctgatg ctttgggaag  21180
tatgttaatt tcatggtaca tgagtggcta tcatactggc tattatatgg taagtaatca  21240
ctcagcatct tttcctgaca atttttttgt agttatgtga ctttgttttg taaatttata  21300
aaatactact tgcttctctc tttatattac taaaaaataa aaataaaaaa atacaactgt  21360
ctgaggctta aattactctt gcattgtccc taagtataat tttagttaat tttaaaaagc  21420
tttcatgcta ttgttagatt attttgatta tacacttttg aattgaaatt atactttttc  21480
taaataatgt tttaatctct gatttgaaat tgattgtagg gaatggaaaa gatgggataa  21540
tttttcataa atgaaaaatg aaattctttt tttttttttt ttttttttga gacggagtct  21600
tgctctgttg cccaggctgg agtgcaatgg cgtgatcttg gctcacagca agctctgcct  21660
cctggattca cgccattctc ctgcctcagc ctcagaggta gctgggacta caggtgcctg  21720
ccaccacgcc tgtctaattt tttgtatttt tttgtaaaga cagggtttca ctgtgttagc  21780
caggatggtc tcaatctcct gaccccgtga tccacccgcc tcggccttcc aagagaaatg  21840
aaattttttt aatgcacaaa gatctggggt aatgtgtacc acattgaacc ttggggagta  21900
tggcttcaaa cttgtcactt tatacgttag tctcctacgg acatgttcta ttgtatttta  21960
gtcagaacat ttaaaattat tttattttat tttatttttt tttttttttt gagacggagt  22020
ctcgctctgt cacccaggct ggagtacagt ggcgcagtct cggctcactg caagctccgc  22080
```

ctcccgggtt cacgccattc tcctgcctca gcctctccga gtagctggga ctacaggcgc 22140
ccgccaccac gcccggctaa tttttttta tttttagtag agacggggtt tcaccgtggt 22200
ctcgatctcc tgacctcgtg atccacccgc ctcggcctcc caaagtgctg ggattacaag 22260
cgtgagccac cgcgcccggc ctaaaattat ttttaaaagt aagctcttgt gccctgctaa 22320
aattatgatg tgatattgta ggcacttgta tttttagtaa attaatatag aagaaacaac 22380
tgacttaaag gtgtatgttt ttaaatgtat catctgtgtg tgcccccatt aatattctta 22440
tttaaaagtt aaggccagac atggtggctt acaactgtaa tcccaacagt ttgtgaggcc 22500
gaggcaggca gatcacttga ggtcaggagt ttgagaccag cctggccaac atgatgaaac 22560
cttgtctcta ctaaaaatac caaaaaaaat ttagccaggc atggtggcac atgcctgtaa 22620
tccgagctac ttgggaggct gtggcaggaa aattgcttta atctgggagg cagaggttgc 22680
agtgagttga gattgtgcca ctgcactcca cccttggtga cagagtgaga ttccatctca 22740
aaaaaagaaa aaggcctggc acggtggctc acacctataa tcccagtact ttgggaggta 22800
gaggcaggtg gatcacttga ggttaggagt tcaggaccag cctggccaac atggtgacta 22860
ctccatttct actaaataca caaaacttag cccagtggcg ggcagttgta atcccagcta 22920
cttgagaggt tgaggcagga gaatcacttg aacctgggag gcagaggttg cagtgagccg 22980
agatcacacc gctgcactct agcctggcca acagagtgag aatttgcgga gggaaaaaaa 23040
agtcacgctt cagttgttgt agtataacct tggtatattg tatgtatcat gaattcctca 23100
ttttaatgac caaaaagtaa taaatcaaca gcttgtaatt tgttttgaga tcagttatct 23160
gactgtaaca ctgtaggctt ttgtgttttt taaattatga aatatttgaa aaaaatacat 23220
aatgtatata taaagtattg gtataattta tgttctaaat aactttcttg agaaataatt 23280
cacatggtgt gcagtttacc tttgaaagta tacaagttgg ctgggcacaa tggctcacgc 23340
ctgtaatccc agcactttgg gaggccaggg caggtggatc acgaggtcag gagatcgaga 23400
ccatcctggc taacatggtg aaaccccgtc tctactaaaa gtacaaaaac aaattagccg 23460
ggcatgttgg cgggcacctt ttgtcccagc tgctcgggag gctgaggcag gagagtggcg 23520
tgaacccagg aggtggagct tgcagtgagc cgagattgtg ccagtgcact ccagcctggg 23580
cgacagagcg agactctgtc tcaaaaaata aaataaaaaa gaaagtatac aagtcagtgg 23640
ttttggtttt cagttatgca accatcacta caatttaaga acattttcat caccccaaaa 23700
agaaaccctg ttaccttcat tttccccagc cctaggcagt cagtacactt tctgtctcta 23760
tgaatttgtc tattttagat attatatata aacggaatta tacgatatgt ggtcttttgt 23820
gtctggcttc tttcacttag catgctattt tcaagattca tccatgctgt agaatgcacc 23880
agtactgcat tccttcttat tgctgaatat tctgttgttt ggttatatca cattttatcc 23940
attcatcagt tcatggacat ttaggttgtt tttatttttg ggctataatg aataatgttg 24000
ctatgaacat tcgtttgtgt tctttttgtt tttttggttt tttgggtttt ttttgttttg 24060
tttttgtttt tgagacagtc ttgctctgtc tcctaagctg gagtgcagtg gcatgatctt 24120
ggcttactgc aagctctgcc tcccgggttc acaccattct cctgcctcag cccgacaagt 24180
agctgggact acaggcgtgt gccaccatgc acggctaatt ttttgtattt ttagtagaga 24240
tggggtttca ccgtgttagc caggatggtc tcgatctcct gacctcgtga tctgcctgcc 24300
taggcctccc aaagtgctgg gattacaggc gtgagccact gcacctggcc ttaagtgttt 24360
ttaatacgtc attgccttaa gctaacaatt cttaaccttt gttctactga agccacgtgg 24420
ttgagatagg ctctgagtct agcttttaac ctctatcttt ttgtcttaga aatctaagca 24480
gaatgcaaat gactaagaat aatgttgttg aaataacata aaataggtta taactttgat 24540
actcattagt aacaaatctt tcaatacatc ttacggtctg ttaggtgtag attagtaatg 24600
aagtgggaag ccactgcaag ctagtataca tgtagggaaa gatagaaagc attgaagcca 24660
gaagagagac agaggacatt tgggctagat ctgacaagaa aaacaaatgt tttagtatta 24720
atttttgact ttaaattttt tttttattta gtgaatactg gtgtttaatg gtctcatttt 24780
aataagtatg acacaggtag tttaaggtca tatattttat ttgatgaaaa taaggtatag 24840
gccgggcacg gtggctcaca cctgtaatcc cagcactttg ggaggccgag gcaggcggat 24900
cacctgaggt cgggagttag agactagcct caacatggag aaaccccgtc tctactaaaa 24960
aaaatacaaa attaggcggg cgtggtggtg catgcctgta atcccagcta ctcaggaggc 25020
tgaggcagga gaattgcttg aacctgggag gtggaggttg cggtgagccg agatcacctc 25080
attgcactcc agcctgggca acaagagcaa aactccatct caaaaaaaaa aaaataaggt 25140
ataagcgggc tcaggaacat cattggacat actgaaagaa gaaaaatcag ctgggcgcag 25200
tggctcacgc cggtaatccc aacactttgg gaggccaagg caggcgaatc acctgaagtc 25260
gggagttcca gatcagcctg accaacatgg agaaaccctg tctctactaa aaatacaaaa 25320
ctagccgggc atggtggcgc atgcctgtaa tcccagctac ttgggaggct gaggcaggag 25380
aattgcttga accgagaagg cggaggttgc ggtgagccaa gattgcacca ttgcactcca 25440
gcctgggcaa caagagcgaa actccgtctc aaaaaaaaaa ggaagaaaaa tattttttta 25500
aattaattag tttatttatt ttttaagatg gagttttgcc ctgtcaccca ggctggggtg 25560
caatggtgca atctcggctc actgcaacct ccgcctcctg ggttcaagtg attctcctgc 25620
ctcagcttcc cgagtagctg tgattacagc catatgccac cacgcccagc cagttttgtg 25680
ttttgttttg ttttttgttt ttttttttttg agagggtgtc ttgctctgtc ccccaagctg 25740
gagtgcagcg gcgcgatctt ggctcactgc aagctctgcc tcccaggttc acaccattct 25800
cttgcctcag cctcccgagt agctgggact acaggtgccc gccaccacac ccggctaatt 25860
tttttgtgtt tttagtagag atggggtttc actgtgttag ccaggatggt ctcgatctcc 25920
tgaccttttg atccacccgc ctcagcctcc ccaagtgctg ggattatagg cgtgagccac 25980
tgtgcccggc ctagtcttgt atttttagta gagtcgggat ttctccatgt tggtcaggct 26040
gttctccaaa tccgacctca ggtgatccgc ccgccttggc ctccaaaagt gcaaggcaag 26100
gcattacagg catgagccac tgtgaccggc aatgttttta aattttttac atttaaattt 26160
tattttttag agaccaggtc tcactctatt gctcaggctg gagtgcaagg gcacattcac 26220
agctcactgc agccttgacc tccagggctc aagcagtcct ctcacctcag tttcccgagt 26280
agctgggact acagtgataa tgccactgca cctggctaat ttttattttt atttatttat 26340
tttttttga gacagagtct tgctctgtca cccaggctgg agtgcagtgg tgtaaatctc 26400
agctcactgc agcctccgcc tcctgggttc aagtgattct cctgcctcaa cctcccaagt 26460
agctgggatt agaggtcccc accaccatgc ctggctaatt ttttgtactt tcagtagaaa 26520
cggggttttg ccatgttggc caggctgttc tcgaactcct gagctcaggt gatccaactg 26580
tctcggcctc ccaaagtgct gggattacag gcgtgagcca ctgtgcctag cctgagccac 26640
cacgccggcc taatttttaa attttttgta gagacagggt ctcattatgt tgcccagggt 26700
ggtgtcaagc tccaggtctc aagtgatccc cctacctccg cctcccaaag ttgtgggatt 26760
gtaggcatga gccactgcaa gaaaacctta actgcagcct aataattgtt ttctttggga 26820

-continued

```
taacttttaa agtacattaa aagactatca acttaatttc tgatcatatt ttgttgaata  26880

aaataagtaa aatgtcttgt gaaacaaaat gctttttaac atccatataa agctatctat  26940

atatagctat ctatatctat atagctattt tttttaactt cctttatttt ccttacaggg  27000

ttttagacaa aatcaaaaag aaggaaggtg ctcacattcc ttaaattaag gagtaagtct  27060

gccagcatta tgaaagtgaa tcttactttt gtaaaacttt atggtttgtg gaaaacaaat  27120

gtttttgaac atttaaaaag ttcagatgtt agaaagttga aaggttaatg taaaacaatc  27180

aatattaaag aattttgatg ccaaaactat tagataaaag gttaatctac atccctacta  27240

gaattctcat acttaactgg ttggttgtgt ggaagaaaca tactttcaca ataaagagct  27300

ttaggatatg atgccatttt atatcactag taggcagacc agcagacttt tttttattgt  27360

gatatgggat aacctaggca tactgcactg tacactctga catatgaagt gctctagtca  27420

agtttaactg gtgtccacag aggacatggt ttaactggaa ttcgtcaagc ctctggttct  27480

aatttctcat ttgcaggaaa tgctggcata gagcagcact aaatgacacc actaaagaaa  27540

cgatcagaca gatctggaat gtgaagcgtt atagaagata actggcctca tttcttcaaa  27600

atatcaagtg ttgggaaaga aaaaaggaag tggaatgggt aactcttctt gattaaaagt  27660

tatgtaataa ccaaatgcaa tgtgaaatat tttactggac tctattttga aaaaccatct  27720

gtaaaagact gaggtggggg tgggaggcca gcacggtggt gaggcagttg agaaaatttg  27780

aatgtggatt agattttgaa tgatattgga taattattgg taattttatg agctgtgaga  27840

agggtgttgt agtttataaa agactgtctt aatttgcata cttaagcatt taggaatgaa  27900

gtgttagagt gtcttaaaat gtttcaaatg gtttaacaaa atgtatgtga ggcgtatgtg  27960

gcaaaatgtt acagaatcta actggtggac atggctgttc attgtactgt tttttttctat  28020

cttctatatg tttaaaagta tataataaaa atatttaatt ttttttaaa             28070


<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3

gtactacact tttaattact                                               20


<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4

tgtatattga tgtcagtact                                               20


<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5

tacattgtct attagtgtat                                               20
```

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
tgactctcaa ttctgttaca 20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
tcacagggct atttctgact 20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
aatcagtcac atatatcaca 20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
tgtaacttta gttaaaatca 20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
ctattaaacc acatttgtaa 20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
actactatgc tttctctatt 20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
ccaccatttc ttgaaactac 20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
tttccaatag ttttaccacc 20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
gtttttgcat aaggatttcc 20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
gtggaaattt ggtttgtttt 20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
tgtggctcag tgtaggtgga 20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
gtattaattc ttatatgtgg 20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ttagttttac acttaggtct 20

<210> SEQ ID NO 19
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 19
acacagttta gagttttagt 20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
gatcacagat ttttctctct 20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
ttataggcaa tccatgatca 20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
catttcagtt tgttcttttg 20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
cccaggcaac aaggccattt 20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
gaacctcggg tgccacccca 20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25

-continued cgtccttgat ttcctcagcg 20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
acacccttgg tgtgtcagcg 20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
ttctgctcta gcctcacacc 20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
ggagagagct agtctctttc 20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
aggacctctc tctgcaggag 20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
atgggaactc ttttcaggac 20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
gcatttcact gtggaatggg 20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
tttataaaaa tgcttgcatt 20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
cttcccatta gctcatttat 20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
tagataagct accccccttcc 20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
tttgctccct atgtgtagat 20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
ggtcctaact ggttttttgc 20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
cagatggcaa cacctggtcc 20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
gattcacgct ctgtgcagat 20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
gcctgcataa taaaaggttg 20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
tcaggccaag gacctgcctg 20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
taagcaatgt ggagtagctc 20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
acaataggaa agagataagc 20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
ttatttagca catgcacaat 20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
tggctccacc tccccttatt 20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
gcatgtccac catggtggct 20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
agctgcacgg agagaaaggg 20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
gcatgttgtg agttgttggg 20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
tcagataagg aagctggaag 20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
gaccttagta catactcaga 20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
gaagtaaaca cagtggacct 20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
gtatgtgaag taaacacagt 20

<210> SEQ ID NO 52

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
gtaaacacag tatgtgaagt 20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
aggtgggtat gtgaagtaaa 20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
atcagcaagc ttcacatacg 20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
ggagcttcct gggtaatcag 20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
agcagctctg gcacagaggg 20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
aaacatgtat aaggaagcag 20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
ggaagatcgg gctgtaaaca 20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
acttctcttc taacaaggag 20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
cagagtcctc ggtagaactt 20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
aagccgatag ttagacagag 20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
aaaaaaagac taggtaagcc 20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
gttttgagag aggaggtaaa 20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
gttttttctt tgatggtttt 20

<210> SEQ ID NO 65
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 65
gaaatctaat ttttcagttt 20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
aatcttaatt ttgctgaaat 20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
tttttaagaa cagaaaatct 20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
acactttggt ttttcatttt 20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
attttctccc ggtttacact 20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
aggtaacttg catgtatttt 20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
aatatcttta tcagataggt 20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
atgtttgctg ggtacaatat 20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
gtttgagagt tcttcatgtt 20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
catcttttaa ttgaattttt 20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
cccggccaac ttacccatct 20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
gattgggatt gcaagtatga 20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
gagcacacgc cacaatgcct 20

<210> SEQ ID NO 78
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 78
agtcttcttg tctcagcctt 20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
ccacctcctg cgctcagtct 20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
tcacacagcc tactgcagcc 20

<210> SEQ ID NO 81
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 81
tcactttcat aatgctgg 18

<210> SEQ ID NO 82
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 82
tgctggcaga cttac 15

<210> SEQ ID NO 83
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 83
cataatgctg gcaga 15

<210> SEQ ID NO 84
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 84
tcataatgct ggcag 15

<210> SEQ ID NO 85
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 85
ttcataatgc tggca 15

<210> SEQ ID NO 86
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 86
tttcataatg ctggc 15

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
attcactttc ataatgctgg 20

<210> SEQ ID NO 88
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 88
ctttcataat gctgg 15

<210> SEQ ID NO 89
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 89
tcataatgct gg 12

<210> SEQ ID NO 90
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 90
actttcataa tgctg 15

<210> SEQ ID NO 91
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 91
ttcataatgc tg 12

<210> SEQ ID NO 92
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 92
cactttcata atgct 15

<210> SEQ ID NO 93
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 93
tttcataatg ct 12

<210> SEQ ID NO 94
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 94
tcactttcat aatgc 15

<210> SEQ ID NO 95
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 95
ctttcataat gc 12

<210> SEQ ID NO 96
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 96
ttcactttca taatg 15

<210> SEQ ID NO 97
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 97
actttcataa tg 12

<210> SEQ ID NO 98
<211> LENGTH: 15

<212> TYPE: DNA
<213> ORGANISM: Artificial sequence
<220> FEATURE:
<223> OTHER INFORMATION: Synthetic oligonucleotide

<400> SEQUENCE: 98
attcactttc ataat 15

<210> SEQ ID NO 99
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 99
cactttcata at 12

<210> SEQ ID NO 100
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 100
gattcacttt cataa 15

<210> SEQ ID NO 101
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 101
tcactttcat aa 12

<210> SEQ ID NO 102
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 102
ttcactttca ta 12

<210> SEQ ID NO 103
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 103
attcactttc at 12

<210> SEQ ID NO 104
<211> LENGTH: 15
<212> TYPE: DNA
<213> ORGANISM: Artificial sequence -continued

```
<220> FEATURE:
<223> OTHER INFORMATION: Synthetic oligonucleotide

<400> SEQUENCE: 104

agtaagattc acttt                                                15
```